(12) United States Patent
Longo et al.

(10) Patent No.: US 11,160,676 B2
(45) Date of Patent: *Nov. 2, 2021

(54) ROTARY HANDLE STENT DELIVERY SYSTEM AND METHOD

(71) Applicant: Vesper Medical, Inc., Malvern, PA (US)

(72) Inventors: Michael A. Longo, Glenmoore, PA (US); Timothy W. O'Neil, King of Prussia, PA (US); Christopher John Turek, West Chester, PA (US)

(73) Assignee: Vesper Medical, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/241,554

(22) Filed: Apr. 27, 2021

(65) Prior Publication Data

US 2021/0244556 A1 Aug. 12, 2021

Related U.S. Application Data

(62) Division of application No. 16/940,533, filed on Jul. 28, 2020, now Pat. No. 10,993,825, which is a
(Continued)

(51) Int. Cl.
*A61F 2/958* (2013.01)
*A61F 2/966* (2013.01)
(Continued)

(52) U.S. Cl.
CPC .......... *A61F 2/966* (2013.01); *A61M 25/0023* (2013.01); *A61M 25/0113* (2013.01);
(Continued)

(58) Field of Classification Search
CPC .... A61F 2/06; A61F 2/91; A61F 2/958; A61F 2/966; A61F 2/07; A61F 2/954;
(Continued)

(56) References Cited

U.S. PATENT DOCUMENTS

| 4,665,918 A | 5/1987 | Garza et al. |
| 5,415,664 A | 5/1995 | Pinchuk |

(Continued)

FOREIGN PATENT DOCUMENTS

| DE | 29717110 U1 | 11/1997 |
| DE | 19819634 | 11/1999 |

(Continued)

OTHER PUBLICATIONS

International Search Report and Written Opinion issued for Application No. PCT/US2019/034371, dated Aug. 19, 2019.
(Continued)

*Primary Examiner* — Vi X Nguyen
(74) *Attorney, Agent, or Firm* — Meunier Carlin & Curfman LLC

(57) ABSTRACT

A delivery device according to principles described herein includes a catheter having three concentric shafts including an inner core, an outer sheath over the inner core and an outer support shaft at least partially extending over the inner core and the outer sheath. A timing belt having a plurality of belt teeth on a surface of the timing belt is coupled to an outer sheath over a medical device or stent on the inner core such that movement of the timing belt link causes movement of the outer sheath from its position over the medical device or stent. The delivery device is actuated by rotation of a thumbwheel a thumbwheel coupled to a barrel having a plurality of teeth such that rotation of the thumbwheel causes movement of the barrel such that the barrel teeth engage the belt teeth to cause movement of the timing belt causing movement of the outer sheath.

11 Claims, 19 Drawing Sheets

Related U.S. Application Data division of application No. 16/599,461, filed on Oct. 11, 2019, now Pat. No. 10,736,762, which is a division of application No. 16/134,287, filed on Sep. 18, 2018, now Pat. No. 10,449,073.

(51) Int. Cl.
*A61M 25/00* (2006.01)
*A61M 25/06* (2006.01)
*A61M 25/01* (2006.01)
*A61F 2/95* (2013.01)

(52) U.S. Cl.
CPC ....... *A61M 25/0662* (2013.01); *A61F 2/9517* (2020.05); *A61M 2025/0004* (2013.01); *A61M 2025/0681* (2013.01)

(58) Field of Classification Search
CPC . A61F 2/95; A61M 25/0113; A61M 25/0023; A61M 25/0662
See application file for complete search history.

(56) References Cited

U.S. PATENT DOCUMENTS

| | | |
|---|---|---|
| 5,417,708 A | 5/1995 | Hall et al. |
| 5,433,723 A | 7/1995 | Lindenberg et al. |
| 5,443,477 A | 8/1995 | Marin et al. |
| 5,458,615 A | 10/1995 | Klemm et al. |
| 5,484,444 A | 1/1996 | Braunschweiler et al. |
| 5,501,654 A | 3/1996 | Failla et al. |
| 5,507,768 A | 4/1996 | Lau et al. |
| 5,571,168 A | 11/1996 | Toro |
| 5,695,499 A | 12/1997 | Helgerson et al. |
| 5,725,534 A | 3/1998 | Rasmussen et al. |
| 5,759,186 A | 6/1998 | Bachmann et al. |
| 5,788,707 A | 8/1998 | Del Toro et al. |
| 5,800,517 A | 9/1998 | Anderson et al. |
| 5,860,998 A | 1/1999 | Robinson et al. |
| 5,906,619 A | 5/1999 | Olson et al. |
| 5,944,727 A | 8/1999 | Ahari et al. |
| 6,019,778 A | 2/2000 | Wilson et al. |
| 6,113,608 A | 9/2000 | Monroe et al. |
| 6,117,140 A | 9/2000 | Munsinger |
| 6,123,720 A * | 9/2000 | Anderson ................ A61F 2/958 606/194 |
| 6,165,166 A | 12/2000 | Samuelson et al. |
| 6,203,550 B1 | 3/2001 | Olson |
| 6,241,758 B1 | 6/2001 | Cox et al. |
| 6,299,635 B1 | 10/2001 | Frantzen |
| 6,302,893 B1 | 10/2001 | Limon et al. |
| 6,402,760 B1 | 6/2002 | Fedida |
| 6,599,296 B1 | 7/2003 | Gillick et al. |
| 6,613,075 B1 | 9/2003 | Healy et al. |
| 6,620,550 B2 | 9/2003 | Christian et al. |
| 6,669,716 B1 | 12/2003 | Gilson et al. |
| 6,702,846 B2 | 3/2004 | Mikus et al. |
| 6,755,854 B2 | 6/2004 | Gillick et al. |
| 6,866,669 B2 | 3/2005 | Buzzard et al. |
| 6,911,039 B2 | 6/2005 | Shiu et al. |
| 6,939,352 B2 | 9/2005 | Buzzard et al. |
| 7,033,368 B2 | 4/2006 | Rourke |
| 7,052,511 B2 | 5/2006 | Weldon et al. |
| 7,105,016 B2 | 9/2006 | Shiu et al. |
| 7,182,779 B2 | 2/2007 | Acosta et al. |
| 7,278,998 B2 | 10/2007 | Gaschino et al. |
| 7,300,456 B2 | 11/2007 | Andreas et al. |
| 7,309,350 B2 | 12/2007 | Landreville et al. |
| 7,326,236 B2 | 2/2008 | Andreas et al. |
| 7,381,216 B2 | 6/2008 | Buzzard et al. |
| D576,725 S | 9/2008 | Shumer et al. |
| 7,419,501 B2 | 9/2008 | Chiu et al. |
| D578,216 S | 10/2008 | Dorn et al. |
| D578,643 S | 10/2008 | Shumer et al. |
| D578,644 S | 10/2008 | Shumer et al. |
| D578,645 S | 10/2008 | Shumer et al. |
| 7,476,244 B2 | 1/2009 | Buzzard et al. |
| 7,550,001 B2 | 6/2009 | Dorn et al. |
| 7,553,322 B2 | 6/2009 | Dorn et al. |
| 7,553,324 B2 | 6/2009 | Andreas et al. |
| 7,660,621 B2 | 2/2010 | Skakoon et al. |
| 7,674,282 B2 | 3/2010 | Wu et al. |
| 7,758,625 B2 | 7/2010 | Wu et al. |
| 7,780,716 B2 | 8/2010 | Pappas et al. |
| 7,794,489 B2 | 9/2010 | Shumer et al. |
| 7,799,065 B2 | 9/2010 | Pappas et al. |
| 7,815,669 B2 | 10/2010 | Matsuoka et al. |
| 7,819,882 B2 | 10/2010 | Rourke |
| 7,892,274 B2 | 2/2011 | Will et al. |
| 7,935,141 B2 | 5/2011 | Randall et al. |
| 7,963,987 B2 | 6/2011 | Melsheimer et al. |
| 7,967,829 B2 | 6/2011 | Gunderson et al. |
| 7,976,574 B2 | 7/2011 | Papp |
| 7,993,384 B2 | 8/2011 | Wu et al. |
| 8,016,870 B2 | 9/2011 | Chew |
| 8,062,344 B2 | 11/2011 | Dorn et al. |
| 8,075,607 B2 | 12/2011 | Melsheimer |
| 8,092,468 B2 | 1/2012 | Hansen |
| 8,157,851 B2 | 4/2012 | Andreas |
| 8,177,831 B2 | 5/2012 | Andreas |
| 8,216,296 B2 | 7/2012 | Wu et al. |
| 8,382,813 B2 | 2/2013 | Shumer |
| D678,512 S | 3/2013 | Bow |
| 8,416,636 B2 | 4/2013 | Carman et al. |
| 8,419,784 B2 | 4/2013 | Matsuoka et al. |
| 8,486,128 B2 | 7/2013 | Jen et al. |
| 8,500,789 B2 | 8/2013 | Wueebbeling et al. |
| 8,500,792 B2 | 8/2013 | Berra |
| 8,585,747 B2 | 11/2013 | Andreas et al. |
| 8,778,006 B2 | 7/2014 | Fargahi et al. |
| 8,784,468 B2 | 7/2014 | Gerdts et al. |
| 8,808,346 B2 | 8/2014 | Jimenez, Jr. et al. |
| 8,828,072 B2 | 9/2014 | Hoffman et al. |
| 8,852,266 B2 | 10/2014 | Brooks et al. |
| 8,864,811 B2 | 10/2014 | Kao |
| 8,888,834 B2 | 11/2014 | Hansen et al. |
| 8,911,487 B2 | 12/2014 | Bennett et al. |
| 8,951,297 B2 | 2/2015 | Kawakita |
| 8,956,398 B2 | 2/2015 | George et al. |
| 8,986,362 B2 | 3/2015 | Snow et al. |
| 8,986,363 B2 | 3/2015 | McHugo et al. |
| 9,039,750 B2 | 5/2015 | Ryan et al. |
| 9,138,315 B2 | 9/2015 | Straubinger et al. |
| 9,149,379 B2 | 10/2015 | Keady et al. |
| 9,301,864 B2 | 4/2016 | Kao |
| 9,314,360 B2 | 4/2016 | Kao |
| 9,320,591 B2 | 4/2016 | Bolduc |
| 9,408,736 B2 | 8/2016 | Loewen |
| 9,421,115 B2 | 8/2016 | Wübbeling et al. |
| 9,445,928 B2 | 9/2016 | Argentine |
| 9,539,130 B2 | 1/2017 | Farag et al. |
| D779,053 S | 2/2017 | Kobida et al. |
| 9,566,179 B2 | 2/2017 | Andreas et al. |
| 9,622,894 B2 | 4/2017 | McGee |
| D786,429 S | 5/2017 | Cummins et al. |
| 9,662,236 B2 | 5/2017 | Masubuchi |
| 9,675,486 B2 | 6/2017 | Jimenez, Jr. et al. |
| D795,425 S | 8/2017 | Cummins |
| 9,744,021 B2 | 8/2017 | Bolduc |
| 9,765,858 B2 | 9/2017 | Kelly |
| 9,849,016 B2 | 12/2017 | Beard et al. |
| 9,872,785 B2 | 1/2018 | Dorn et al. |
| 9,878,127 B2 | 1/2018 | Damm et al. |
| 9,901,468 B2 | 2/2018 | Harada |
| 9,913,741 B2 | 3/2018 | Melsheimer et al. |
| 9,918,835 B2 | 3/2018 | Guyenot et al. |
| 9,974,677 B2 | 5/2018 | Costello |
| 9,974,678 B2 | 5/2018 | Cummins |
| 10,016,292 B2 | 7/2018 | Senness et al. |
| 10,441,449 B1 | 10/2019 | Longo et al. |
| 10,987,239 B2 * | 4/2021 | Longo .................... A61F 2/966 |
| 2001/0004696 A1 | 6/2001 | Roberts et al. |
| 2001/0012944 A1 | 8/2001 | Bicek et al. |
| 2001/0027323 A1 | 10/2001 | Sullivan et al. |

(56) References Cited

U.S. PATENT DOCUMENTS

| | | |
|---|---|---|
| 2001/0047150 A1 | 11/2001 | Chobotov |
| 2002/0007138 A1 | 1/2002 | Wilk et al. |
| 2002/0007206 A1 | 1/2002 | Bui et al. |
| 2002/0029075 A1 | 3/2002 | Leonhardt |
| 2002/0065545 A1 | 5/2002 | Leonhardt |
| 2002/0128707 A1 | 9/2002 | Kavteladze |
| 2002/0151953 A1 | 10/2002 | Chobotov et al. |
| 2003/0009174 A1 | 1/2003 | Smith |
| 2003/0036791 A1 | 2/2003 | Philipp et al. |
| 2003/0040789 A1 | 2/2003 | Colgan et al. |
| 2003/0045893 A1 | 3/2003 | Ginn |
| 2003/0050686 A1 | 3/2003 | Raeder-Devens et al. |
| 2003/0074045 A1 | 4/2003 | Buzzard et al. |
| 2003/0120331 A1 | 6/2003 | Chobotov et al. |
| 2003/0149469 A1 | 8/2003 | Wolinsky et al. |
| 2003/0149476 A1 | 8/2003 | Damm et al. |
| 2003/0149478 A1 | 8/2003 | Figulla et al. |
| 2003/0153941 A1 | 8/2003 | Rourke |
| 2003/0167087 A1 | 9/2003 | Piplani et al. |
| 2003/0191516 A1 | 10/2003 | Weldon et al. |
| 2004/0006380 A1 | 1/2004 | Buck et al. |
| 2004/0093056 A1 | 5/2004 | Johnson et al. |
| 2004/0106977 A1 | 6/2004 | Sullivan et al. |
| 2004/0153137 A1 | 8/2004 | Gaschino et al. |
| 2004/0167619 A1 | 8/2004 | Case et al. |
| 2004/0181239 A1 | 9/2004 | Dorn et al. |
| 2004/0193243 A1 | 9/2004 | Mangiardi et al. |
| 2004/0199240 A1 | 10/2004 | Dorn |
| 2004/0210188 A1 | 10/2004 | Glines et al. |
| 2005/0027345 A1 | 2/2005 | Horan et al. |
| 2005/0033403 A1 | 2/2005 | Ward et al. |
| 2005/0038493 A1 | 2/2005 | Feeser |
| 2005/0060016 A1 | 3/2005 | Wu et al. |
| 2005/0080476 A1 | 4/2005 | Gunderson et al. |
| 2005/0090887 A1 | 4/2005 | Pryor |
| 2005/0090890 A1 | 4/2005 | Wu et al. |
| 2005/0137686 A1 | 6/2005 | Salahieh et al. |
| 2005/0149159 A1* | 7/2005 | Andreas ................ A61F 2/966 623/1.11 |
| 2005/0149160 A1 | 7/2005 | McFerran |
| 2005/0182475 A1 | 8/2005 | Jen et al. |
| 2005/0232961 A1 | 10/2005 | Lowe et al. |
| 2005/0256562 A1 | 11/2005 | Clerc et al. |
| 2005/0273151 A1 | 12/2005 | Fulkerson et al. |
| 2005/0288763 A1 | 12/2005 | Andreas et al. |
| 2006/0009833 A1 | 1/2006 | Chobotov et al. |
| 2006/0020321 A1 | 1/2006 | Parker |
| 2006/0142833 A1 | 6/2006 | Von Oepen et al. |
| 2006/0212105 A1 | 9/2006 | Dorn et al. |
| 2006/0229711 A1 | 10/2006 | Yan et al. |
| 2006/0247661 A1 | 11/2006 | Richards et al. |
| 2006/0259124 A1 | 11/2006 | Matsuoka et al. |
| 2006/0286145 A1 | 12/2006 | Horan et al. |
| 2007/0055340 A1 | 3/2007 | Pryor |
| 2007/0060999 A1 | 3/2007 | Randall et al. |
| 2007/0088421 A1 | 4/2007 | Loewen |
| 2007/0100440 A1 | 5/2007 | Figulla et al. |
| 2007/0112355 A1 | 5/2007 | Salahieh et al. |
| 2007/0118079 A1 | 5/2007 | Moberg et al. |
| 2007/0142906 A1 | 6/2007 | Figulla et al. |
| 2007/0156224 A1 | 7/2007 | Cioanta et al. |
| 2007/0162127 A1 | 7/2007 | Peterman et al. |
| 2007/0168014 A1 | 7/2007 | Jimenez et al. |
| 2007/0185558 A1 | 8/2007 | Hartley |
| 2007/0191925 A1 | 8/2007 | Dorn |
| 2007/0213813 A1 | 9/2007 | Von Segesser et al. |
| 2007/0219617 A1 | 9/2007 | Saint |
| 2008/0082154 A1 | 4/2008 | Tseng et al. |
| 2008/0154293 A1 | 6/2008 | Taylor |
| 2008/0188920 A1 | 8/2008 | Moberg et al. |
| 2008/0255660 A1 | 10/2008 | Guyenot et al. |
| 2009/0005760 A1 | 1/2009 | Cartledge et al. |
| 2009/0024133 A1 | 1/2009 | Keady et al. |
| 2009/0024137 A1 | 1/2009 | Chuter et al. |
| 2009/0171428 A1 | 7/2009 | Hansen |
| 2009/0177264 A1 | 7/2009 | Ravenscroft |
| 2009/0210046 A1 | 8/2009 | Shumer et al. |
| 2009/0216310 A1 | 8/2009 | Straubinger et al. |
| 2009/0234443 A1 | 9/2009 | Ottma et al. |
| 2009/0312831 A1 | 12/2009 | Dorn |
| 2010/0004606 A1 | 1/2010 | Hansen et al. |
| 2010/0004730 A1 | 1/2010 | Benjamin et al. |
| 2010/0036472 A1 | 2/2010 | Papp |
| 2010/0076541 A1 | 3/2010 | Kumoyama |
| 2010/0125280 A1 | 5/2010 | Molloy |
| 2010/0137967 A1 | 6/2010 | Atlani et al. |
| 2010/0168756 A1 | 7/2010 | Dorn et al. |
| 2010/0168834 A1 | 7/2010 | Ryan et al. |
| 2010/0174290 A1 | 7/2010 | Wueebbeling et al. |
| 2010/0292779 A1 | 11/2010 | Straubinger et al. |
| 2011/0056064 A1 | 3/2011 | Malewicz et al. |
| 2011/0190862 A1 | 8/2011 | Bashiri et al. |
| 2011/0190865 A1 | 8/2011 | McHugo et al. |
| 2011/0288626 A1 | 11/2011 | Straubinger et al. |
| 2011/0295363 A1 | 12/2011 | Girard et al. |
| 2011/0319989 A1 | 12/2011 | Lane et al. |
| 2012/0022631 A1 | 1/2012 | Costello |
| 2012/0022632 A1 | 1/2012 | Hoffman et al. |
| 2012/0022635 A1 | 1/2012 | Yamashita |
| 2012/0029607 A1 | 2/2012 | McHugo et al. |
| 2012/0041450 A1 | 2/2012 | Awtar et al. |
| 2012/0053671 A1 | 3/2012 | McHugo et al. |
| 2012/0116493 A1 | 5/2012 | Harada |
| 2012/0123516 A1 | 5/2012 | Gerdts et al. |
| 2012/0158117 A1 | 6/2012 | Ryan |
| 2012/0209175 A1 | 8/2012 | Moelgaard-Nielsen |
| 2012/0209366 A1 | 8/2012 | Sudo et al. |
| 2012/0226341 A1 | 9/2012 | Schreck et al. |
| 2012/0265288 A1 | 10/2012 | Jones et al. |
| 2012/0310321 A1 | 12/2012 | Beach et al. |
| 2012/0330401 A1 | 12/2012 | Sugimoto et al. |
| 2013/0013057 A1 | 1/2013 | Salahieh et al. |
| 2013/0018451 A1 | 1/2013 | Grabowski et al. |
| 2013/0079864 A1 | 3/2013 | Boden et al. |
| 2013/0085562 A1 | 4/2013 | Rincon et al. |
| 2013/0103130 A1 | 4/2013 | Lubinski et al. |
| 2013/0184805 A1 | 7/2013 | Sawada |
| 2013/0211493 A1 | 8/2013 | Wubbeling et al. |
| 2013/0268048 A1 | 10/2013 | Watson et al. |
| 2013/0268049 A1 | 10/2013 | Munsinger et al. |
| 2013/0304189 A1 | 11/2013 | Shimoyama |
| 2013/0338752 A1 | 12/2013 | Geusen et al. |
| 2014/0025155 A1 | 1/2014 | Masubuchi |
| 2014/0081252 A1 | 3/2014 | Bowe et al. |
| 2014/0107673 A1 | 4/2014 | Snyder et al. |
| 2014/0121674 A1 | 5/2014 | Staunton |
| 2014/0121755 A1 | 5/2014 | Farag et al. |
| 2014/0180380 A1 | 6/2014 | Kelly |
| 2014/0257454 A1 | 9/2014 | McGee |
| 2014/0257459 A1 | 9/2014 | Masakazu |
| 2014/0276682 A1 | 9/2014 | Hendrick et al. |
| 2014/0277037 A1 | 9/2014 | Grace et al. |
| 2014/0277321 A1 | 9/2014 | Grace |
| 2014/0277349 A1 | 9/2014 | Vad |
| 2014/0343601 A1 | 11/2014 | Abbott et al. |
| 2014/0343660 A1 | 11/2014 | Shimoyama |
| 2015/0025615 A1 | 1/2015 | Brooks et al. |
| 2015/0051688 A1 | 2/2015 | Cummins |
| 2015/0057739 A1 | 2/2015 | Costello |
| 2015/0057741 A1 | 2/2015 | Ryan |
| 2015/0065280 A1 | 3/2015 | Kelly |
| 2015/0094794 A1 | 4/2015 | Cummins et al. |
| 2015/0105796 A1 | 4/2015 | Grace |
| 2015/0119800 A1 | 4/2015 | Neoh et al. |
| 2015/0127092 A1 | 5/2015 | Straubinger et al. |
| 2015/0148894 A1 | 5/2015 | Damm et al. |
| 2015/0230954 A1 | 8/2015 | McHugo |
| 2015/0238315 A1 | 8/2015 | Rabito et al. |
| 2015/0238730 A1 | 8/2015 | Corman et al. |
| 2015/0250631 A1 | 9/2015 | Cummins et al. |
| 2015/0265445 A1 | 9/2015 | Weber et al. |
| 2015/0282881 A1 | 10/2015 | Beard et al. |
| 2015/0297378 A1 | 10/2015 | Senness et al. |
| 2015/0335333 A1 | 11/2015 | Jones et al. |

(56) References Cited

U.S. PATENT DOCUMENTS

| | | |
|---|---|---|
| 2015/0343121 A1 | 12/2015 | Kobida et al. |
| 2016/0074184 A1 | 3/2016 | Cummins et al. |
| 2016/0074189 A1 | 3/2016 | Cummins |
| 2016/0123441 A1 | 5/2016 | Gillick et al. |
| 2016/0135972 A1 | 5/2016 | Vad et al. |
| 2016/0135975 A1 | 5/2016 | Shimoyama |
| 2016/0158010 A1 | 6/2016 | Lim et al. |
| 2016/0158049 A1 | 6/2016 | Dooley |
| 2016/0213465 A1 | 7/2016 | Girard et al. |
| 2016/0235568 A1 | 8/2016 | Green |
| 2016/0262883 A1 | 9/2016 | Sandstrom |
| 2016/0303734 A1 | 10/2016 | Bowles et al. |
| 2017/0035590 A1 | 2/2017 | Watson et al. |
| 2017/0348100 A1 | 2/2017 | Lane et al. |
| 2017/0056156 A1 | 3/2017 | Ryan |
| 2017/0095236 A1 | 4/2017 | Sharma et al. |
| 2017/0095330 A1 | 4/2017 | Malewicz et al. |
| 2017/0095922 A1 | 4/2017 | Licht et al. |
| 2017/0172773 A1 | 6/2017 | Gong et al. |
| 2017/0216063 A1 | 8/2017 | Bessho |
| 2017/0348087 A1 | 12/2017 | Chobotov et al. |
| 2018/0021132 A1 | 1/2018 | Ottma et al. |
| 2018/0080533 A1 | 3/2018 | Awtar |
| 2018/0098849 A1 | 4/2018 | Yellin et al. |
| 2018/0133006 A1 | 5/2018 | Jones et al. |
| 2018/0133007 A1 | 5/2018 | Prabhu |
| 2018/0147076 A1 | 5/2018 | Cummins et al. |
| 2018/0153693 A1 | 6/2018 | Copeland et al. |
| 2018/0153694 A1 | 6/2018 | Wilson et al. |
| 2018/0206976 A1 | 7/2018 | Cartledge et al. |

FOREIGN PATENT DOCUMENTS

| | | |
|---|---|---|
| DE | 102013015896 | 3/2015 |
| EP | 3354237 | 8/2018 |
| JP | 2008132027 | 6/2008 |
| JP | 2012187177 | 10/2012 |
| KR | 101685325 | 12/2016 |
| WO | 2008034793 | 3/2008 |
| WO | 2008124844 | 10/2008 |
| WO | 2017052414 | 3/2017 |
| WO | 2018107123 | 6/2018 |

OTHER PUBLICATIONS

International Search Report and Written Opinion issued for Application No. PCT/US2019/034376, dated Oct. 30, 2019.

* cited by examiner

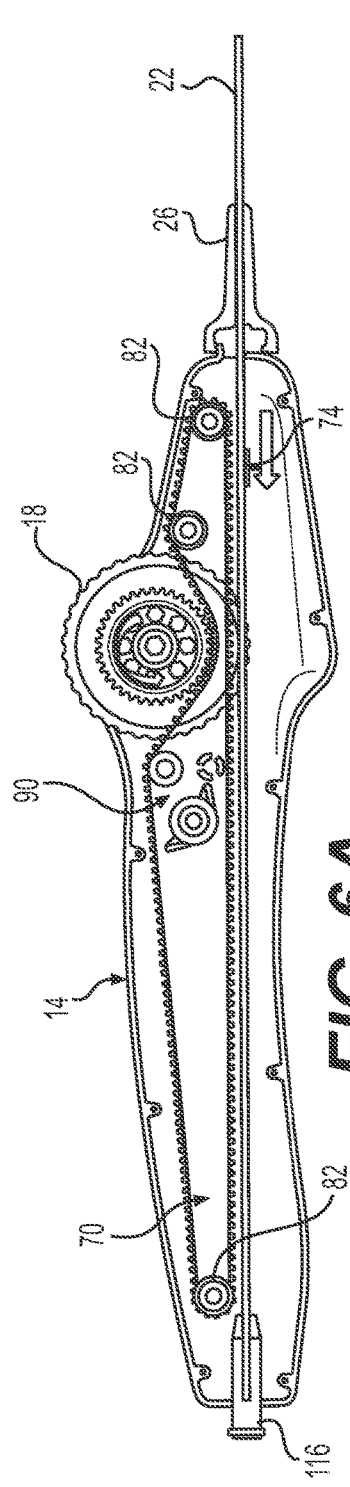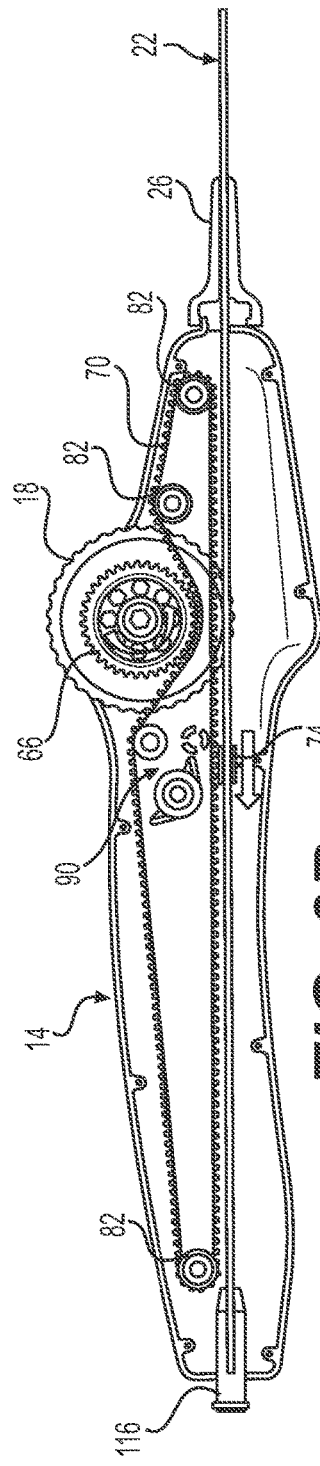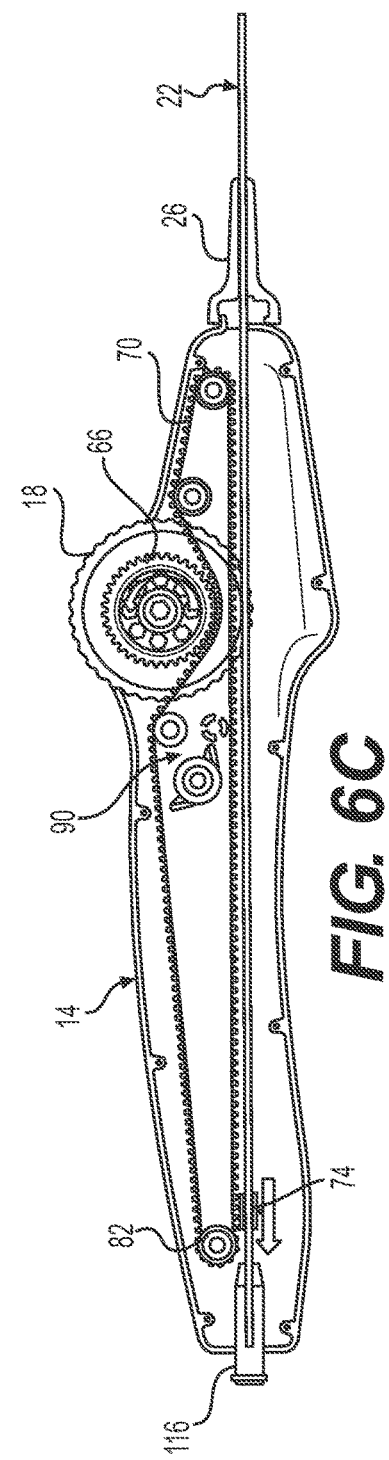

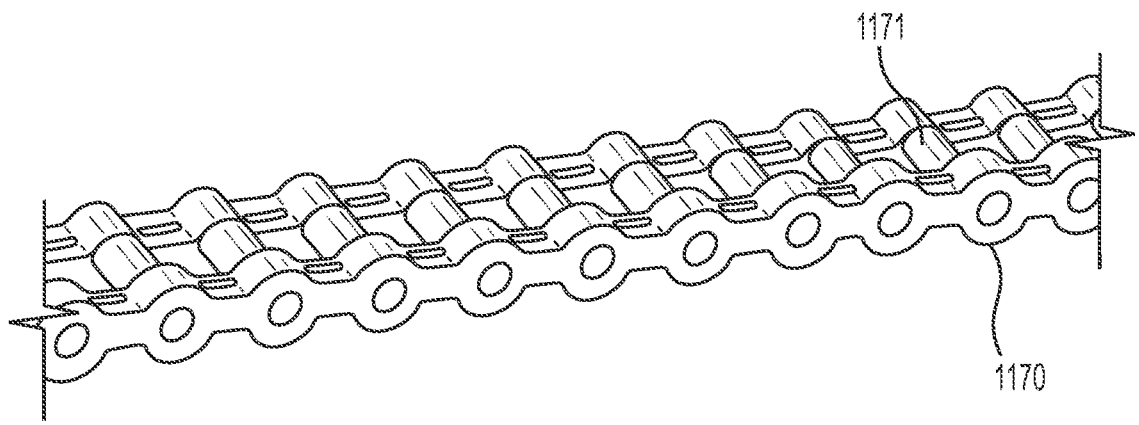
FIG. 20
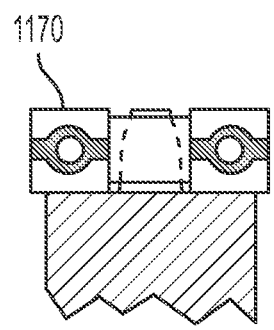 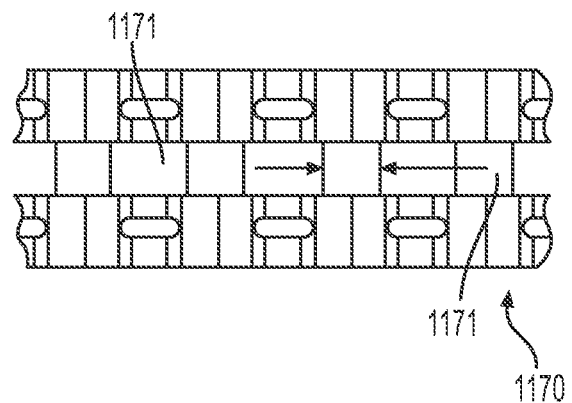
FIG. 21

ROTARY HANDLE STENT DELIVERY SYSTEM AND METHOD

This application is a divisional application of U.S. application Ser. No. 16/940,533, filed Jul. 28, 2020, pending, which is a divisional application of U.S. patent application Ser. No. 16/599,461, filed Oct. 11, 2019, now U.S. Pat. No. 10,736,762, issued Aug. 11, 2020, which is a divisional application of U.S. patent application Ser. No. 16/134,287, filed Sep. 18, 2018, now U.S. Pat. No. 10,449,073, issued Oct. 22, 2019, the disclosures of which are incorporated herein by reference in their entirety.

BACKGROUND OF THE INVENTION

Field of the Invention

Embodiments of the present invention relate to a stent delivery device, specifically a single-handed thumbwheel driven delivery handle.

Background

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Self-expanding stents, as well as balloon expandable stents, may also be used to treat various issues with the vascular system, including, but not limited to May-Thurner Syndrome and Deep Vein Thrombosis.

Stents are usually delivered in a compressed condition to the target site and then, deployed at that location into an expanded condition to support the vessel and help maintain it in an open position. The delivery system used to implant or deploy at the stent target site in the diseased vessel using a delivery system.

Stents are commonly delivered using a catheter delivery system. A common type of delivery system for delivering a self-expanding stent is called a pull back delivery system. This type of delivery system utilizes two catheters or shafts which are concentrically arranged, one around another. The stent is carried axially around the distal end of the inner catheter or shaft. The stent is carried to the delivery site on the distal end of the delivery device, held in its compressed delivery position by the outer shaft or catheter. Once at the desired placement site, the outer shaft is pulled back, releasing the stent to self-expand.

BRIEF SUMMARY OF THE INVENTION

Accordingly, the present invention is directed to a rotary handle stent delivery system and method that obviates one or more of the problems due to limitations and disadvantages of the related art.

In accordance with the purpose(s) of this invention, as embodied and broadly described herein, this invention, in one aspect, relates to a delivery device according to principles described herein including a catheter having three concentric shafts including an inner core, an outer sheath over the inner core and an outer support shaft; a timing belt having a plurality of belt teeth on a surface of the timing belt; a timing belt link coupled to the outer sheath such that movement of the timing belt link causes movement of the outer sheath; a barrel having barrel teeth corresponding to belt teeth; and a thumbwheel coupled to the barrel such that rotation of the thumbwheel causes movement of the barrel such that the barrel teeth engage the belt teeth to cause movement of the timing belt causing movement of the outer sheath.

In another aspect, a system for delivery of an intraluminal stent according to principles described herein includes a delivery device with a catheter having three concentric shafts including an inner core having the intraluminal stent thereon; an outer sheath over the stent in an unexpanded state on the inner core therein, the outer sheath holding the stent in an unexpanded state, the outer sheath translatable coaxially over the inner core and the intraluminal stent; and an outer support shaft at least partially extending over the inner core and the outer sheath; a timing belt having a plurality of belt teeth on a surface of the timing belt; a timing belt link coupled to the outer sheath such that movement of the timing belt link causes movement of the outer sheath to expose the intraluminal stent; a barrel having barrel teeth corresponding to belt teeth; and a thumbwheel coupled to the barrel such that rotation of the thumbwheel causes movement of the barrel such that the barrel teeth engage the belt teeth to cause movement of the timing belt causing movement of the outer sheath.

In yet another aspect, a method of delivering an medical device to a body according to principles described herein uses a delivery device with a catheter having three concentric shafts including an inner core, an outer sheath over the inner core and an outer support shaft; a timing belt having a plurality of belt teeth on a surface of the timing belt; a timing belt link coupled to the outer sheath such that movement of the timing belt link causes movement of the outer sheath; a barrel having barrel teeth corresponding to belt teeth; a thumbwheel coupled to the barrel such that rotation of the thumbwheel causes movement of the barrel such that the barrel teeth engage the belt teeth to cause movement of the timing belt causing movement of the outer sheath; and a medical device over an outer diameter of the inner core; the method includes rotating the thumbwheel in a predetermined direction to cause the timing belt to move in direction associated with the predetermined direction of thumbwheel rotation to cause the timing belt link to move the outer sheath in a desired direction; and deploying the medical device from a distal end of the inner core to the body as the outer sheath moves in the desired direction.

Additional advantages will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Further embodiments, features, and advantages of the rotary handle stent delivery system and method, as well as the structure and operation of the various embodiments of the rotary handle stent delivery system and method, are described in detail below with reference to the accompanying drawings.

It is to be understood that both the foregoing general description and the following detailed description are exemplary and explanatory only and are not restrictive of the invention as claimed.

BRIEF DESCRIPTION OF THE DRAWINGS

The accompanying figures, which are incorporated herein and form part of the specification, illustrate a rotary handle stent delivery system and method. Together with the description, the figures further serve to explain the principles of the rotary handle stent delivery system and method described herein and thereby enable a person skilled in the pertinent art to make and use the rotary handle stent delivery system and method.

FIGS. 6(a)-(c) are cross-sectional views of the delivery device according to principles described herein and illustrate motion of the timing belt link and outer sheath upon movement of the thumbwheel.

FIG. 20 illustrates an alternative type of posi-drive belt that could be used in the delivery assembly according to principles described herein.

FIG. 21 illustrates an alternative type of posi-drive belt that could be used in the delivery assembly according to principles described herein

DETAILED DESCRIPTION

Reference will now be made in detail to embodiments of the rotary handle stent delivery system and method with reference to the accompanying figures. Various embodiments disclosed herein illustrate a device and associated method for delivering expandable stents or other medical devices to implant or deploy a stent or other medical device to a target site in the diseased vessel.

Figure 1A:
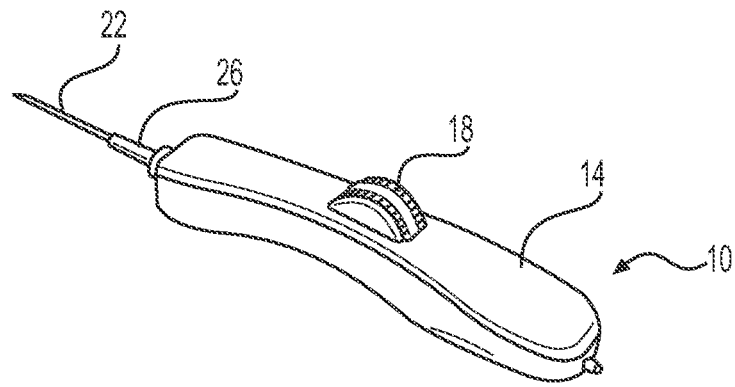
FIGS. 1(a)-(c) show various embodiments of a stent delivery handle according to principles described herein.
Figure 1B:
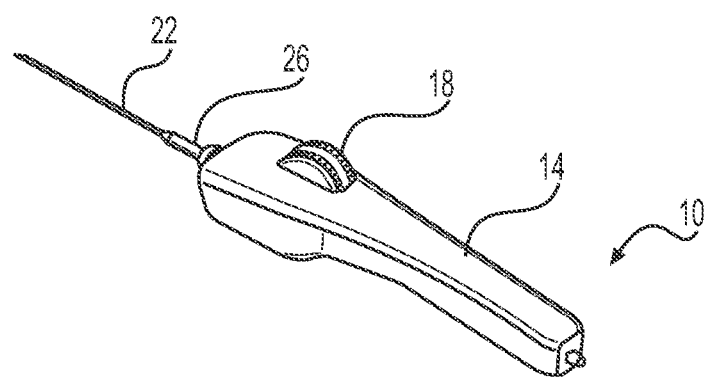
Figure 1C:
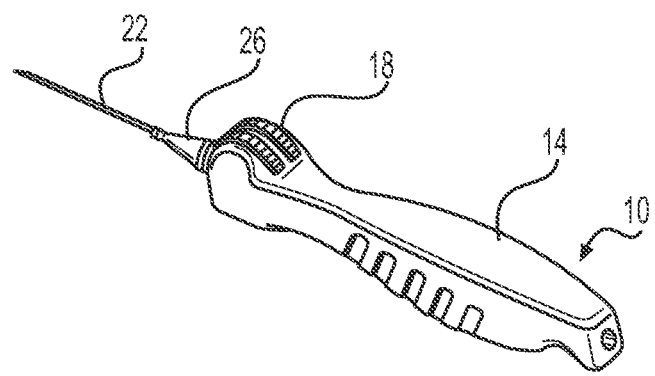

FIGS. 1(a)-(c) show various embodiments of a stent delivery handle according to principles described herein. As illustrated, the handle 10 includes a housing 14 and a thumbwheel/thumbwheel assembly 18, with a triaxial catheter 22 extending therefrom. The catheter may extend through strain relief 26 from the housing 10. The strain relief 26 can take any form, such as being made of polyolefin or other similar flexible material.

Figure 2:
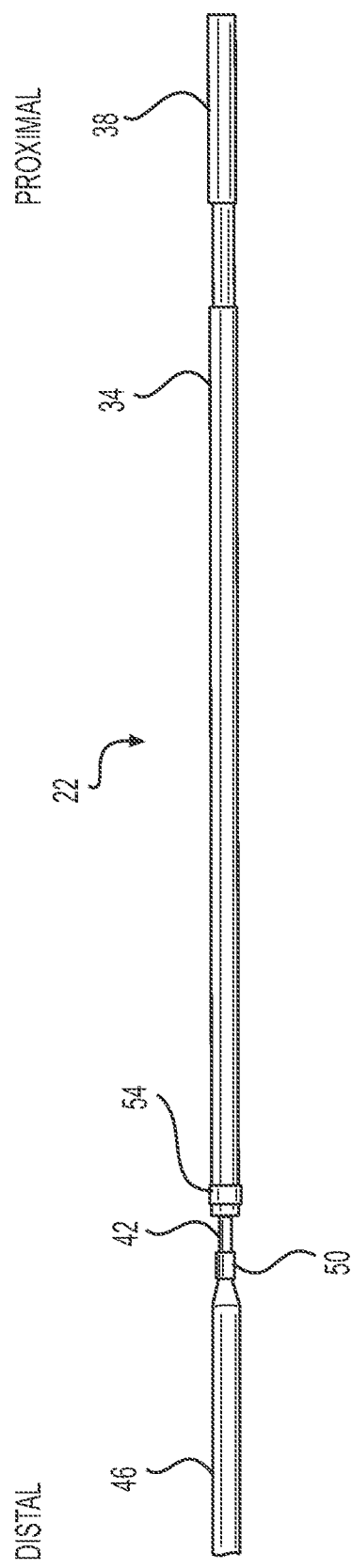
FIG. 2 illustrates an exemplary catheter configuration according to principles described herein.

Referring to FIG. 2, the catheter 22 includes three concentric or "coaxial" tubes/shafts (a triaxial design): inner core 42, outer sheath 34 and an outer support shaft 38. The outer sheath 34 may be tapered or stepped, as illustrated in FIG. 2, or may not be tapered, depending on the application. The outer support shaft 38 may be a PEEK (polyaryletheretherketone) tubing extrusion or other similar structure. The outer support shaft 38 can be manufactured from any semi-rigid material. PEEK exhibits good mechanical properties to provide support for the smaller diameter of the outer sheath and is flexible. PEEK is also an off-the-shelf component. A material other than PEEK may be used to form the outer support sheath, and the invention described herein is not limited to PEEK for use in the outer support shaft 38. Functionally, the outer support shaft 38 and inner core are fixed in position at the proximal end of the delivery system and the outer sheath translates coaxially over the inner core and inside the outer support shaft 38. A medical device such as a self-expanding stent (not shown) is held in a reduced delivery configuration for insertion and transport through a body lumen to a predetermined site for deployment. The stent (not shown) is carried axially around the inner core 42 and is held in its reduced delivery configuration by the outer sheath 34. The inner core 42 may be a braid reinforced tube that extends from the distal end to the proximal end of the device. In some embodiments, the inner core 42 may extend from the very distal end to the very proximal end (e.g. all the way from end to end). The inner diameter of the tube of the inner core 42 is sized for tracking over a guidewire and the outer diameter of the tube of the inner core 42 at the distal end is where the stent (not show) will be crimped between to inner core band markers (50). The outer support shaft 38 is used to stiffen the delivery device so that the arc of the inner core 42 will not change outside of the body when the outer sheath 34 is pulled back to release the stent (not shown) to self-expand. The outer support shaft 38 is connected to the handle 10 at the proximal end of the device, which stiffens the delivery system and reduces friction at the treatment insertion site so that the inner core 42 will not be urged forward as the middle shaft/outer sheath 34 is pulled backward. As illustrated in FIG. 2, the catheter 22 may include a distal tip 46. The inner core 42 may further include at least one inner core marker band 50 such that self-expanding stent is crimped and loaded at the distal end of the catheter and located over the inner core between two inner core marker bands 50 (only one is shown in FIG. 2) to prevent axial movement of the stent. The crimped and loaded self-expanding stent is circumferentially constrained by the outer sheath 34. The outer sheath 34 may also include an outer sheath marker band 54.

The triaxial design allows for more optimal delivery system stability and accurate placement during stent deployment as compared to a traditional 2-coaxial delivery system. The system in introduced into the body at an access location thorough an introducer sheath with hemostasis valve. Where the stent delivery system enters the introducer sheath into the body friction is generated at the hemostasis valve. Therefore, during deployment of a traditional 2-axis system as the outer sheath is being retracted, it wants to move relative to the introducer sheath due to friction, resulting in the inner core pushing out the stent versus retracting the outer sheath. The operator needs to compensate for this and move the entire delivery catheter while deploying the stent to maintain consistent placement during deployment. With long high radial force stents (such as venous stents) this can result in distal/proximal movement (accordion effect) of the entire delivery system during deployment of the stent and can result in inaccurate deployment or malposition of the stent. The triaxial design mitigates this effect as the outer support shaft 38 is inserted through the introducer sheath and therefore the friction between the outer sheath translation and introducer sheath hemostasis valve is eliminated.

Figure 3:
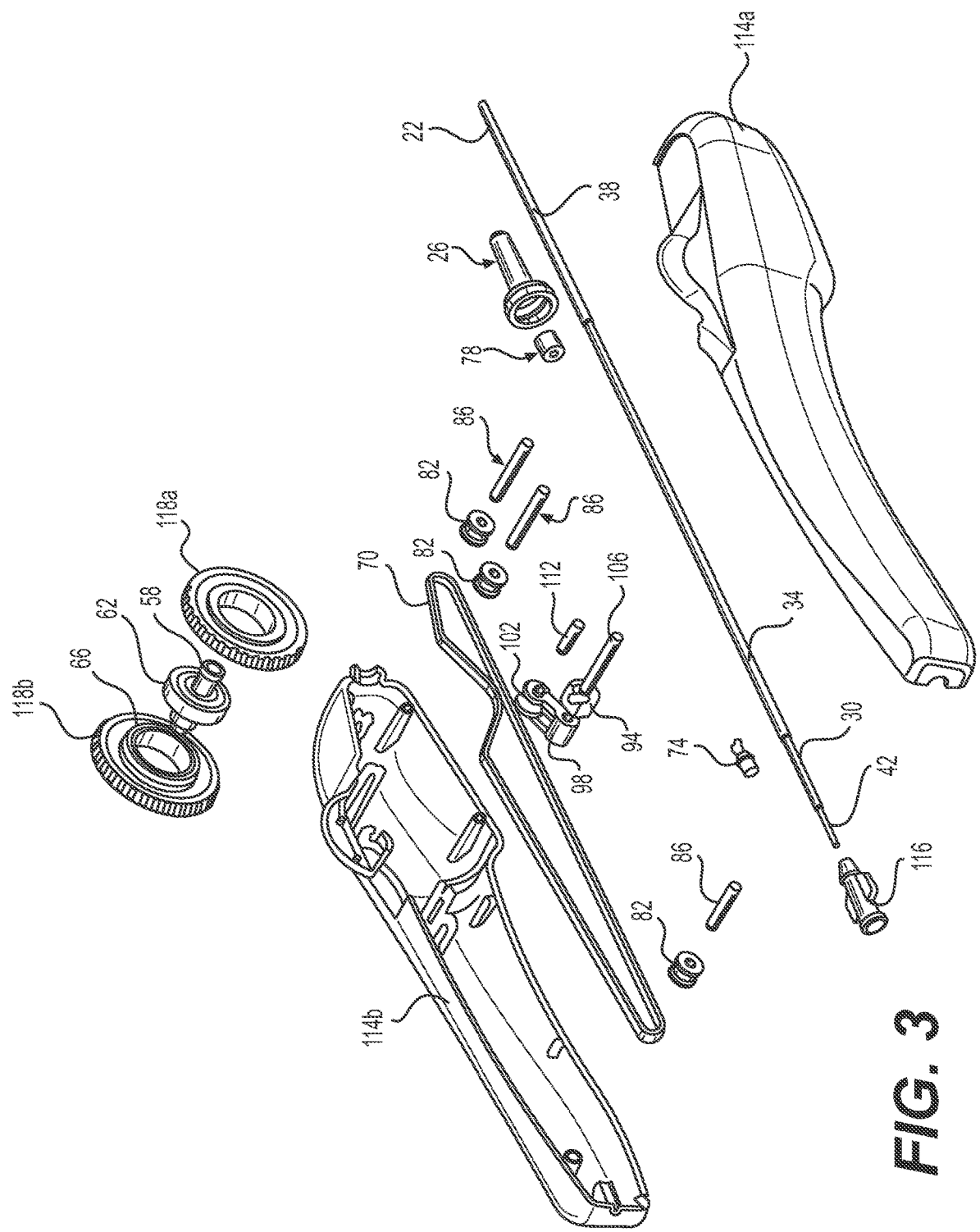
FIG. 3 illustrates is an exploded view of features of a delivery handle according to principles described herein.

FIG. 3 illustrates an exploded view of features of a delivery handle according to principles described herein. The exemplary embodiment illustrated in FIG. 3 includes a two-part housing 114a and 114b, where the respective two parts 114a and 114b may be snap fit together for assembly. The thumbwheel 18 may comprise two wheels 118a and 118b, an axle 58, and a bearing 62. The wheels 118a and 118b may include teeth on an inner barrel 66 thereof. Although only one inner barrel is shown in FIG. 3 on wheel 118b, wheel 118a may also include an inner barrel with teeth. The teeth on the inner barrel 66 are sized to correspond with teeth on a timing belt 70. A timing belt link 74 connects the outer sheath 34 to the timing belt 70. The housing may include a bushing 78, which may be a separate component or may be integral to the housing 14. The bushing may be formed of PEEK or other suitable material. The exemplary handle of FIG. 3 further includes at least one idler pulley 82 for tensioning and guiding the timing belt. Also shown in FIG. 3 idler pulley axles 86 corresponding to the idler pulleys 82 of the embodiment of FIG. 3. The exemplary delivery handle of FIG. 3 further includes a tensioner assembly 90, the tensioner assembly 90 including a torsion spring 94, a tensioner arm 98, a tensioner pulley 102, a tensioner arm axle 106 and a tensioner pulley axle 112. In the presently described embodiment, the timing belt has teeth on one side (outer diameter or periphery) of the belt and the inner diameter (inner surface) is smooth or substantially smooth or flat. The smooth or flat surface of the timing belt 70 contacts the idler pulleys 82 and the tensioner pulley 102.

In the exemplary embodiment of FIG. 3, the outer support shaft 38 is fixed to the handle housing 14, and both the inner core 42 and outer sheath 34 are contained within the inner diameter of the outer shaft 38. The inner core 42 will be bonded at the proximal end along with a metal (e.g., stainless steel) shaft 30 to a female luer 116, which is coupled to or clamped into the handle body 14. In an aspect of the present invention, the metal shaft 30 may be bonded to the outer diameter of the inner core 42 to provide support/rigidity at the proximal end where the inner core 42 is unsupported in the handle body 10. The support of the metal shaft 30 over the inner core 42 mitigates potential deformation/buckling of proximal unsupported inner core 42 during stent deployment. As the outer sheath 34 is pulled back to release/deploy the stent, the inner core 42 is put into compression, therefore the unsupported proximal end of the inner core could deform. The bonded metal shaft 30 provides support and column strength to unsupported proximal inner core 42. The metal shaft 30 may be sized such that is slides over the outer diameter of the inner core 42 and through the inner diameter of the outer sheath 34. The metal shaft 30 does not impact the inner diameter of the inner core 42, so a guidewire (not shown) can still pass through entire assembly. A material other than metal may be used to for the support shaft, and the invention described herein is not limited to metal for use in the support shaft 30.

The outer sheath 34 is coupled to or bonded to the timing belt link 74 to deliver the stent by retracting the outer sheath 34 by movement of the thumbwheel, which in turn engages the teeth of the timing belt 70 via the inner barrel 66 and the teeth on the inner barrel 66. The metal shaft 30 that is coupled to or bonded to the inner core 42/female luer 116 is a guide rail that the outer sheath 34 and timing belt link 74 move proximally over during deployment.

Figure 4:
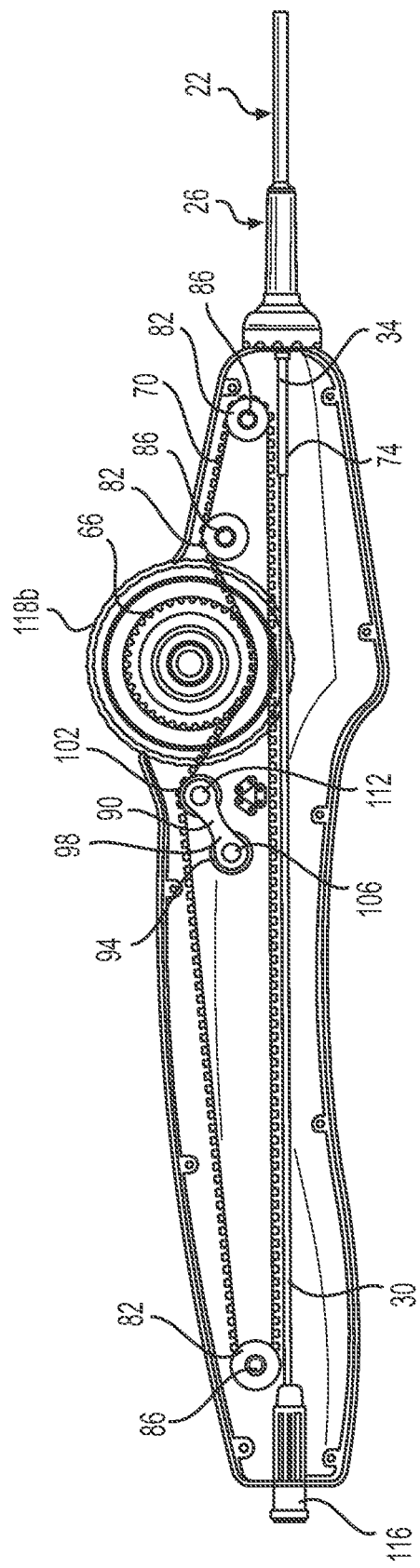
FIG. 4 is cross-sectional view of an assembled handle according to principles described herein

FIG. 4 is a cross-sectional view of an assembled handle according to principles described herein. The exemplary embodiment illustrated in FIG. 4 shows one part 114b of the two-part housing, where the respective two parts may be snap fit together for assembly. Other assembly methods may be used to mate the two parts together such as welding, bonding, gluing or other method. It is contemplated that each side of the two part housing is symmetrical and complementary, but such configuration is not required. The parts of the thumbwheel assembly 18 may be formed by molding, such as injection molding. The housing 14 may be unitary.

FIG. 4 illustrates one wheel of the thumbwheel assembly 18 that may comprise two wheels 118a and 118b, an axle 58, and a bearing 62. The bearing may include a ball bearing with an inner and outer grooved bearing race. The bearing serves to reduce rotational friction between the thumbwheel and the axle and may be eliminated if the frictional forces are acceptable. An acetal bushing or other method of friction reduction may be used in place of the bearing 62.

The wheels 118a and 118b may include teeth on an inner barrel 66 thereof. Although only one inner barrel is shown in FIG. 4 on wheel 118b, wheel 118a may also include an inner barrel with teeth. The teeth on the inner barrel 66 are sized to correspond with a timing belt 70. The inner barrel may be formed by molding, such as injection molding, and the teeth may be formed as part of the molding or other method such that the teeth are integral to the inner barrel 66. In another aspect, the teeth may be separable from the inner barrel 66.

As shown, the timing belt link 74 connects the outer sheath 34 to the timing belt 70. The exemplary handle of FIG. 4 further includes at least one idler pulley 82 for tensioning and guiding the timing belt 74. Also shown in FIG. 4 idler pulley axles 86 corresponding to the idler pulleys 82 of the embodiment of FIG. 4. The exemplary delivery handle of FIG. 4 further includes a tensioner assembly 90, the tensioner assembly 90 including a torsion spring 94, a tensioner arm 98, a tensioner pulley 102, a tensioner arm axle 106 and a tensioner pulley axle 112. In the exemplary embodiment of FIG. 4, the outer support shaft 38 is fixed to the handle housing 14, and both the inner core 42 and outer sheath 34 are contained within the inner diameter of the outer shaft 38. The inner core 42 will be bonded at the proximal end along with a metal (e.g., stainless steel) shaft 30 to a female luer 116, which is coupled to or clamped into the handle body 14.

Figure 5:
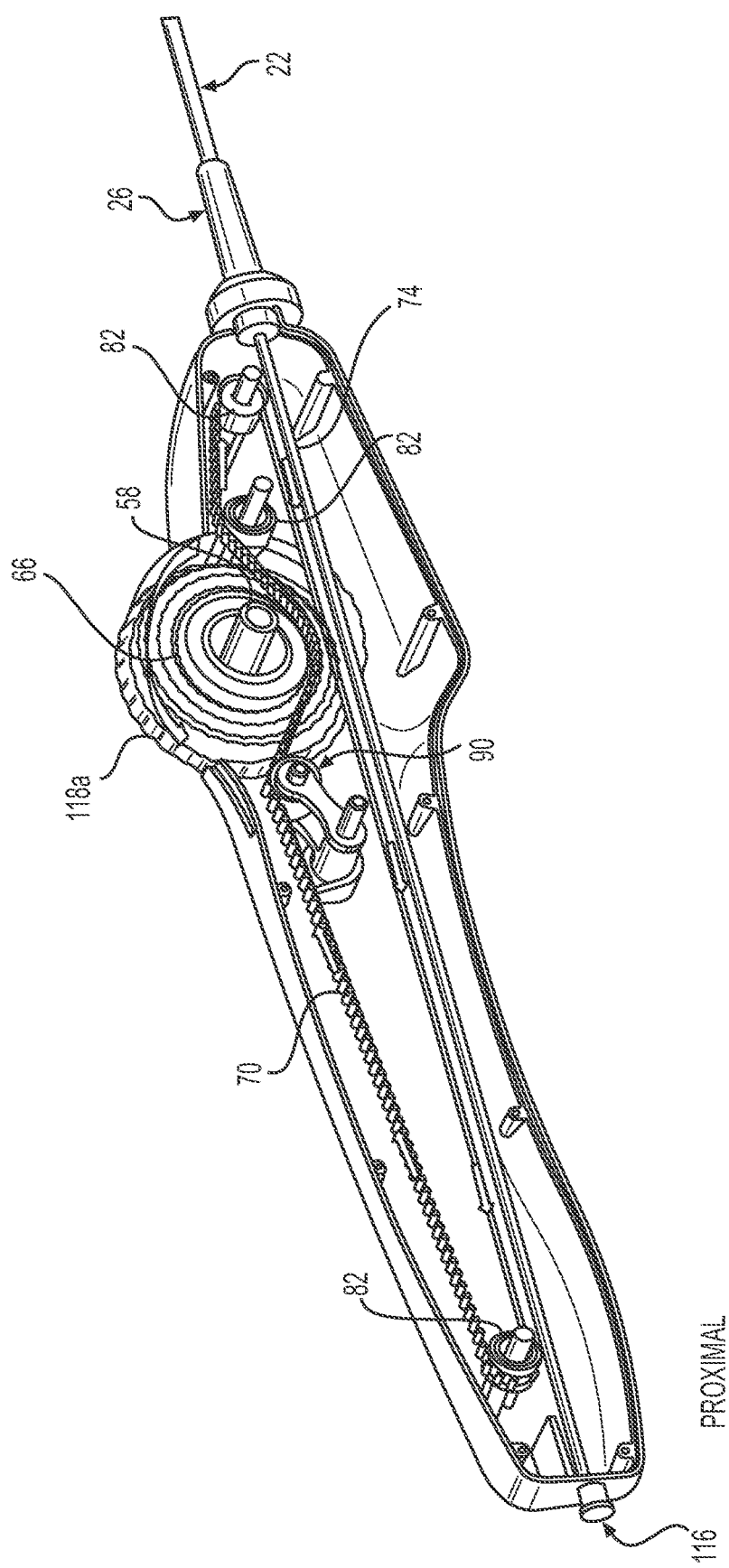
FIG. 5 is a cross-sectional view illustrating motion of the thumbwheel and the timing belt.

FIG. 5 further illustrates motion of the thumbwheel 18, timing belt 70 and timing belt link 74 for deployment of a stent according to principles described herein. As illustrated in FIG. 5, outer sheath 34 is translated proximally over guide tube/inner core 42 by the timing belt 70 by rotating the thumbwheel in the direction of the arrow. The timing belt 70 is driven by an operator via dual thumbwheel assembly 18, which may comprise integrally molded gear teeth, the pitch and shape of which correspond to teeth of the timing belt 70 for synchronizing/engaging the timing belt and causing movement of the timing belt to cause movement of the timing belt link, which is coupled to the outer sheath 34 to cause movement thereof for unsheathing (deploying) a stent provided therein. The diameter of the inner barrel 66, number of teeth on timing belt 70, and the pitch/frequency of the teeth on the timing belt 70 may each be adjusted/modified to allow for variable mechanical advantage during stent deployment and variable translation ratio. In addition, variable speed delivery may also be achieved by actuating the thumbwheel assembly 18 at the desired speed.

In the embodiment illustrated in FIG. 5, rotation of the portion thumbwheel 18 external to the handle proximally (in the direction of the arrow) causes an upper portion of the portion of the timing belt adjacent the portion of the thumbwheel internal to the handle to move distally (in the direction of the arrow). The timing belt 70 extends around an idler pulley 82 such that a portion of the timing belt 70 adjacent the timing belt link 74 move proximally (in the direction of the arrow), engaging the timing belt link 74 to move the timing belt link 74 proximally, which moves the outer sheath 34 coupled thereto proximally, thereby unsheathing the stent for deployment. Movement may be reversed for re-sheathing of catheter following stent deployment.

FIGS. 6(*a*)-(*c*) are cross-sectional views of the delivery device according to principles described herein and illustrates motion of the timing belt link 74 and outer sheath 34 upon movement of the thumbwheel 18 counterclockwise in the context of FIGS. 6(*a*)-(*c*). It should be appreciated that the direction of thumbwheel rotation described herein is described in the context of the cross-section provide, but that it is contemplated that the portion of thumbwheel external to the handle 14 will be rotated rearward (in a proximal direction). It is also contemplated that the configuration of the timing belt 70 may be adjusted (for example, looped over the thumbwheel) to modify the direction of rotation of the thumbwheel corresponding to the proximal movement (retraction) of the outer sheath 34.

As shown in FIG. 6(*a*), in an introducing position, the timing belt link is at a distal end of the handle housing. As the thumbwheel 18 is actuated in a predetermined direction, e.g. in the context of the cross-section shown, counterclockwise, the timing belt link/shuttle 74 moves proximally. Because the timing belt link/shuttle 74 is coupled to the outer sheath 34, the outer sheath moves proximally with the timing belt link/shuttle to expose a stent or other medical device mounted on the inner core 42 (not shown). FIG. 6(*b*) illustrates the positioning of the timing belt link/shuttle in a partially deployed position (e.g. the stent is partially deployed (not shown)). As the thumbwheel 18 is further rotated in a timing belt link/shuttle 74 further translates proximally to allow for full deployment of the stent or medical devices from the of the inner core 42, as shown in FIG. 6(*c*). In the embodiment here described, the thumbwheel 18 is actuated such that the upper side (external portion) of the thumbwheel is rotated proximally to cause the timing belt link/shuttle 74 to transit proximally. It is appreciated that the configuration/path of the timing belt 70 may be configured such that a distal rotation of the upper side (external portion) of the thumbwheel 18 may cause the timing belt link/shuttle 74 to transit proximally to cause the outer sheath 34 to retract from the inner core 42 to allow deployment of the medical device (not shown).

Figure 7:
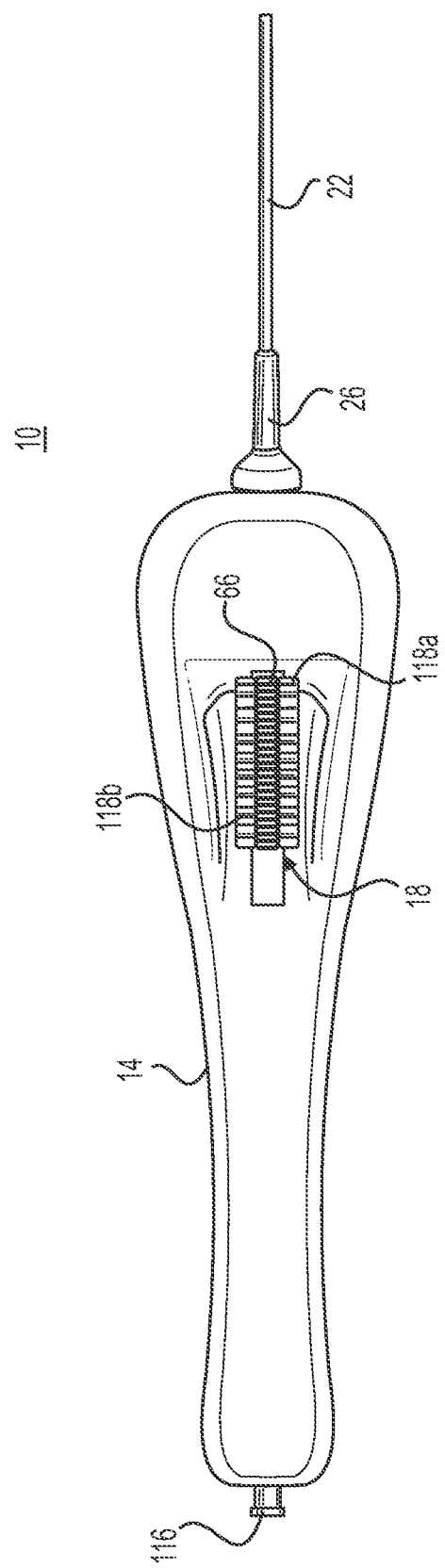
FIG. 7 is a top view of the delivery device according to principles described herein.

Although not shown in the figures, the thumbwheel may be a single thumbwheel with appropriate teeth corresponding to the teeth of the timing belt. As illustrated in the top view of FIG. 7, a thumbwheel comprising two wheels allows for a balanced design in which the catheter may exit the handle at a central portion of the distal end of the handle. FIG. 7 shows an assembled handle 10 and housing 14, and a thumbwheel assembly 18 having a first thumbwheel 118*a* and a second thumbwheel 118*b* separated by inner barrel 66. This configuration facilitates operation of the delivery device by holding the handle from either the left or the right side, allowing for comparable operation regardless of whether the operator is left or right handed.

Figure 8:
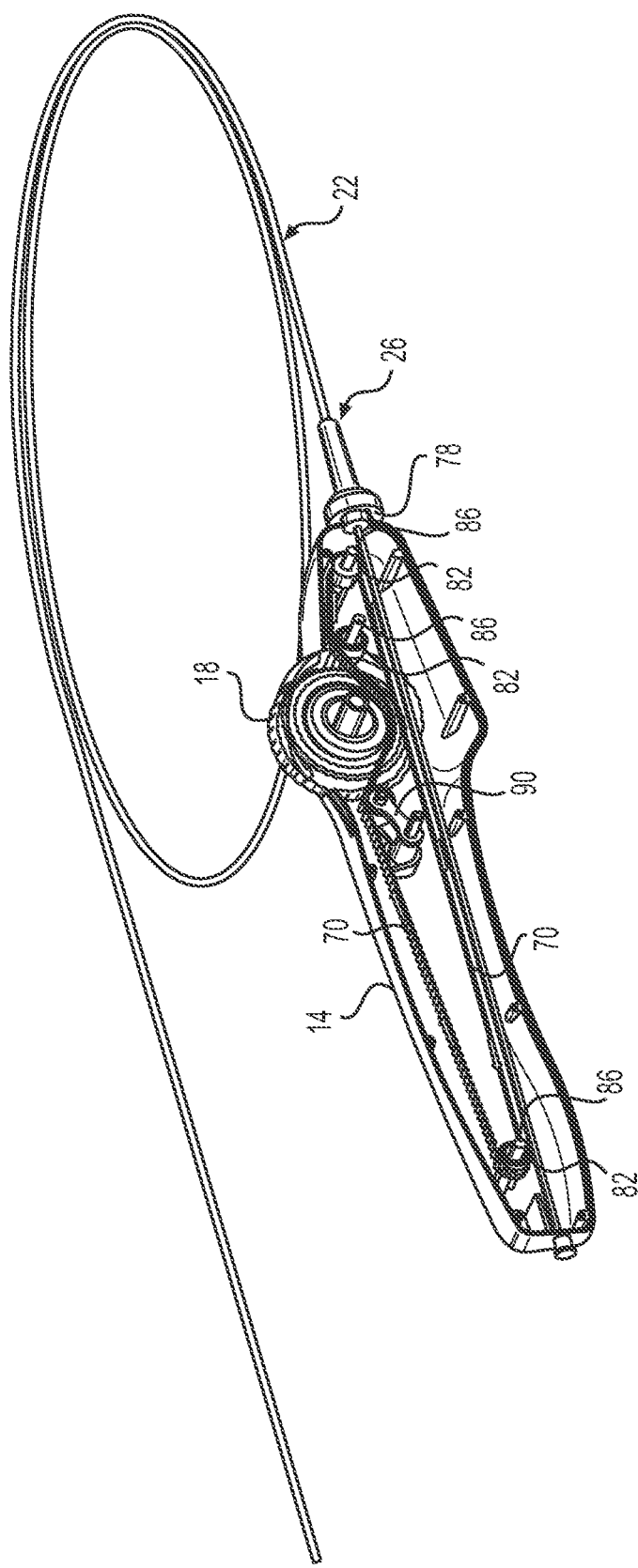
FIG. 8 illustrates a perspective view of the delivery device according to principles described herein, including the catheter device.
Figure 18A:
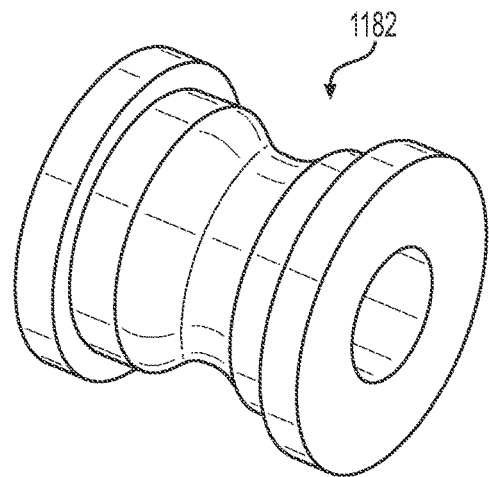
FIGS. 18(a) and 18(b) illustrates a idler that may be used with the posi-drive belt illustrated in FIG. 17.
Figure 18B:
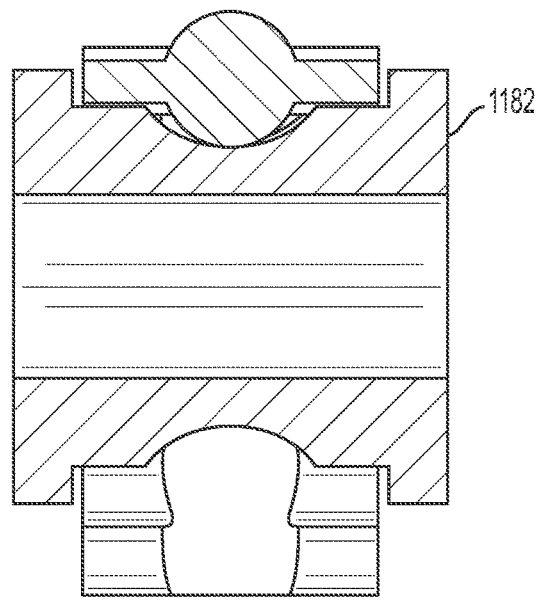

FIG. 8 illustrates a perspective view of the delivery device according to principles described herein, including the catheter device. As shown in FIG. 8, the timing belt 70 extends around idler pulleys 82 and the tensioner pulley 102 of tensioner 90. The tensioner pulley 102 is coupled to the torsion spring 94 via the tensioner arm 98. Tension is maintained on the timing belt by torsion spring 94 on tensioner arm axle 106, which urges the tensioner pulley 102 into contact with the timing belt 70 via the tensioner arm 98. An example idler pulley 82 is illustrated in FIGS. 18(*a*) and 18(*b*).

Figure 9:
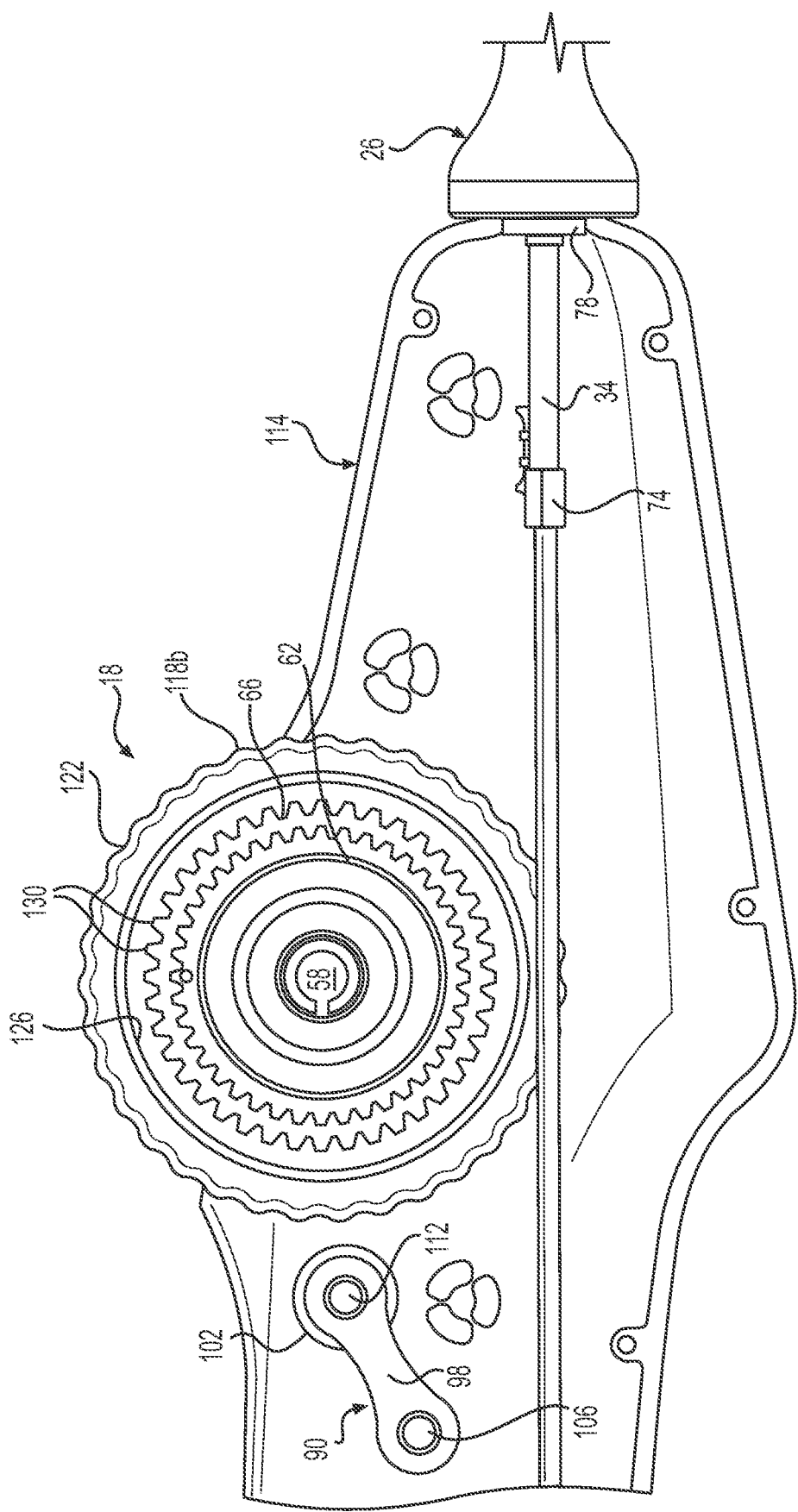
FIG. 9 is a cross-sectional line drawing showing detail of an exemplary embodiment of the thumbwheel assembly.

FIG. 9 is a cross-sectional line drawing showing detail of an exemplary embodiment of the thumbwheel assembly 18 and the timing belt link 74. As illustrated in FIG. 9, one part 118*b* of a two-part thumbwheel 18 has an outer surface 122 that may be textured for ease of use. The thumbwheel part 118*b* may also include an inner surface or rim 126. An inner barrel 66 extends from the thumbwheel part 118*b* and has a plurality of barrel teeth 130 thereon. The barrel teeth 130 on the inner barrel 66 are sized to correspond with a timing belt (not shown). Although not illustrated, the barrel teeth 130 may have a standard periodicity (pitch) or may have a variable periodicity (pitch) such that actuation of the thumbwheel assembly may cause movement of the timing belt (not shown) and thus translation of outer sheath 34 at a first rate when barrel teeth of a first periodicity engage the timing belt (not shown) and at a second rate when barrel teeth of a second periodicity engage the timing belt (not shown). Such variable rate may be imparted by having different spacing/periodicity/pitch of the teeth on the timing belt instead of or in addition to having different spacing/periodicity/pitch of the barrel teeth 130 on the inner barrel 66. FIG. 9 further illustrates the thumbwheel bearing 62 and the thumbwheel axle 58.

A safety locking feature (not shown) may be incorporated in the handle design such to mitigate inadvertent actuation of the handle during transit and storage. The safety locking feature may be a removal/disposal or toggle feature that engages the teeth on the inner barrel to lock it in place and prevent rotation. The safety locking feature may also be a feature that engages the timing belt link to prevent its translation.

Figure 10:
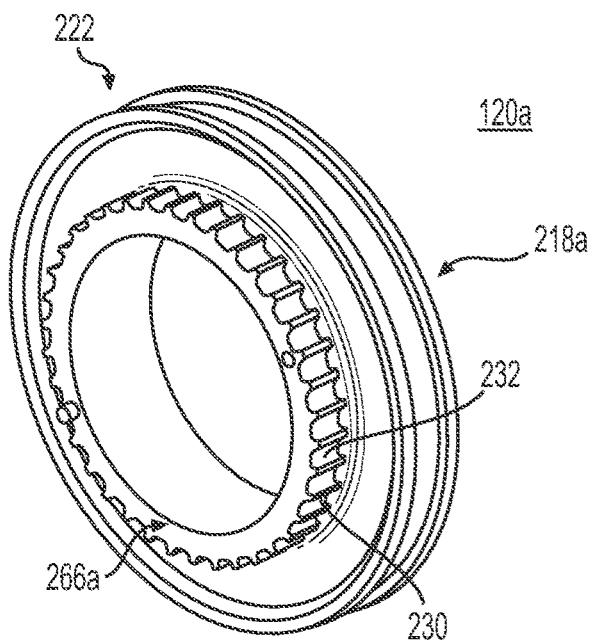
FIG. 10 illustrates a portion of a thumbwheel according to principles described herein.

FIG. 10 illustrates a portion of a thumbwheel according to principles described herein. The thumbwheel may comprise two wheel parts 120*a* and 120*b*, as shown in at least FIG. 3. As illustrated in FIG. 10, one of the wheel parts 120*a* may be a body 222 including a portion of the thumbwheel 218*a* (e.g. the outer circumference a portion of which extends through the housing such that a user can rotate the thumbwheel to actuate the device) and a portion of the barrel 266*a* (e.g. a portion of which engages the timing belt (not shown) to move the timing belt). The wheel part 120*a* may be unitary such that the thumbwheel portion 218*a* that extends through the housing and the barrel portion 266*a* may be unitary (e.g., they can be formed in a single molding process). The other wheel (not shown) may also include both a portion of the thumbwheel for actuation and a portion of the barrel such that the two "wheels" may be fit together to form the thumbwheel and barrel assembly. In other words, the other wheel may be a mirror image of the wheel described above. In some configurations, the two "wheels" may be the same, such that only one mold may be used. It is also possible that the thumbwheel assembly is formed as a single unit to include both the barrel and the thumbwheel portions.

Figure 11:
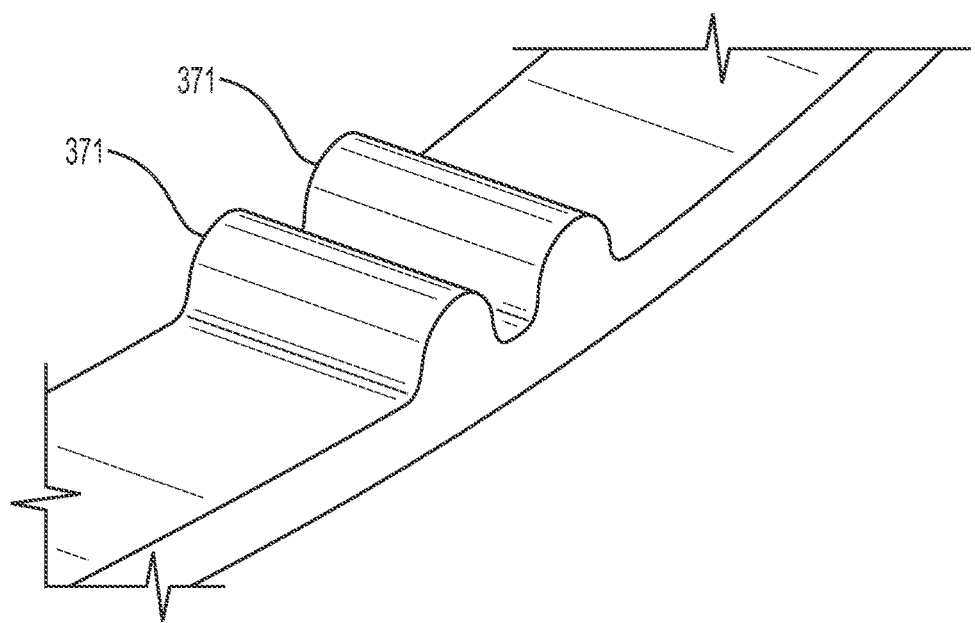
FIG. 11 illustrates exemplary belt teeth.

As shown in the exemplary embodiment of FIG. 10, the exemplary wheel part barrel portion 266a includes grooves 232 that are substantially equally/evenly spaced to engage the pitch of a corresponding timing belt (not shown). The timing belt includes a plurality of substantially equally/evenly spaced teeth along a face of the belt to engage the grooves 232 on the corresponding barrel 266. FIG. 11 illustrates exemplary belt teeth. The belt shown in FIG. 11 is exemplary only, as it only shows two teeth, but the belt is designed to have teeth along enough of the belt to sufficiently deploy the stent.

Figure 12:
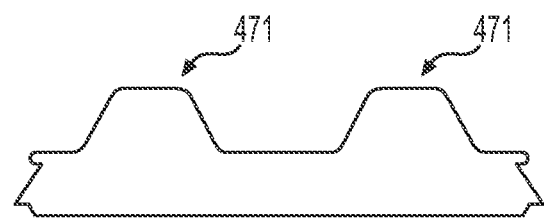
FIG. 12 illustrates exemplary belt teeth.

Exemplary belt teeth are shown in FIG. 12. As illustrated in FIG. 12, exemplary belt teeth 471 may have a tapered shape with a flat top, e.g., trapezoidal cross-section, to allow for engagement with the barrel teeth 230 or groove 232. Although a trapezoidal cross section is shown, the teeth are not so limited and may be of any cross section that may engage with the barrel teeth sufficiently to allow belt movement to be actuated by barrel rotation. Other possible shapes, without limitation, include: without limitation, include circular, cylindrical, diamond, square, triangular or any variation thereof.

Figure 13:
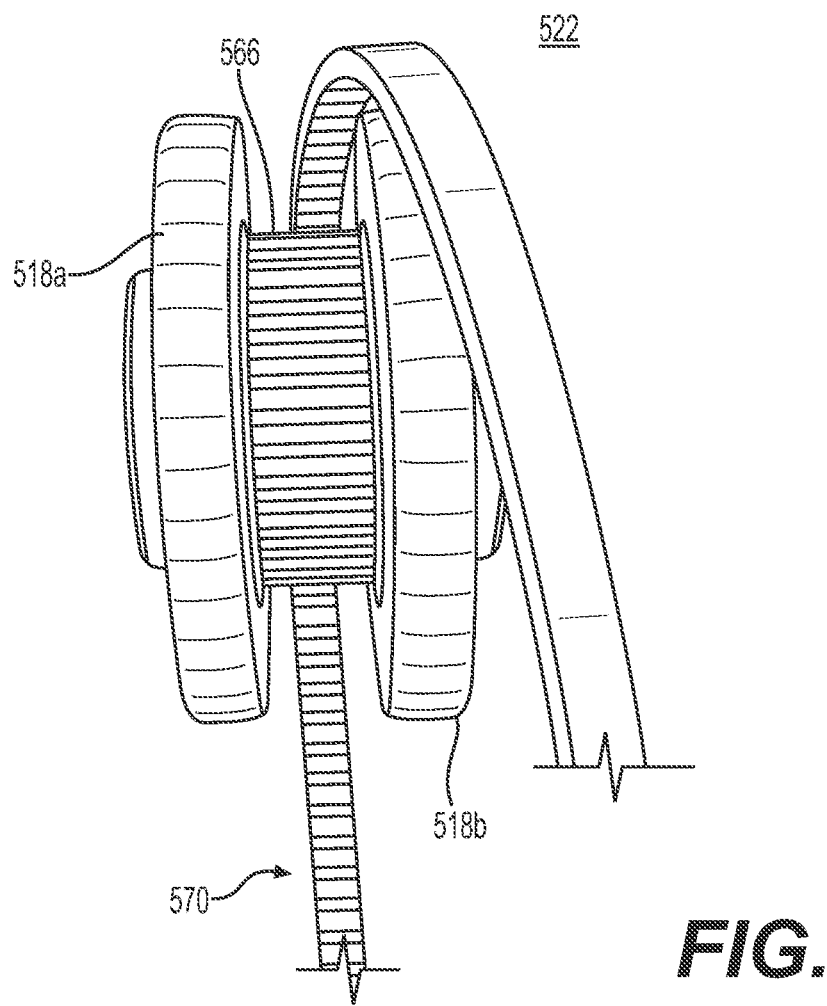
FIG. 13 shows a prototype thumbwheel/barrel assembly with a timing belt.

In some cases, the timing belt may be looped over the barrel of the thumbwheel to provide more full engagement of the timing belt with the barrel. In this embodiment, a longer timing belt would be used such approximately 360 degrees of engagement may be achieved between the belt and the barrel. FIG. 13 shows a prototype thumbwheel/barrel assembly 522 with a timing belt 570 where the barrel width is sized to allow for the timing belt 570 shown to be looped around the barrel 566 at least one full revolution. For example, cylindrical surface of the barrel 566 with the teeth could be sized to be twice the width of the timing belt 570 to accommodate the timing belt 570 being looped over the barrel 566 twice. The widened barrel 566 might thus have that the two parts of the thumbwheel 518a and 518b be spaced further apart than if the timing belt only engaged the barrel 566 at a fraction of the circumference of the barrel 566. In one aspect, the thumbwheel outer cylindrical edge could be modified to cause some over the outer edge of each portion of the thumbwheel to "overhang" the barrel to allow a more surface area for user engagement.

In another aspect, the barrel may be substantially cylindrical, such that an end of the cylinder has a set of teeth and/or grooves and the other end of the cylinder has a set of teeth and/or grooves. The barrel may further comprise a core region between the ends having teeth and/or grooves. The barrel with such teeth may be a unitary piece or may be two parts that are fitted together. The ends of the substantially cylindrical barrel are spaced apart sufficient to receive a central portion of a belt therebetween. A timing belt for use with the barrel thus described has a plurality of protrusions on opposite sides of the belt, for example, extending perpendicular to a pitch axis of the belt. The protrusions are designed to engage corresponding teeth and/or grooves on the barrel to transfer torque from the barrel to the belt, which is coupled to the outer sheath as described above, to cause deployment of the stent. The barrel may further comprise a groove therein for receiving a portion of the belt, such that the barrel itself may not be substantially cylindrical.

The barrel assembly may be formed by placing two disks with appropriately spaced teeth on circumferential edge thereof a distance apart sufficient to allow teeth on each of the disks to engage teeth of the timing belt. A cylindrical core may extend between each of the disks. The cylindrical core and "disks" may, actually be a unitary piece that is substantially cylindrical, such that an end of the cylinder has a set of teeth and/or grooves and the other end of the cylinder has a set of teeth and/or grooves with a core region therebetween. The teeth and/or grooves on the two ends may be substantially aligned.

Figure 14:
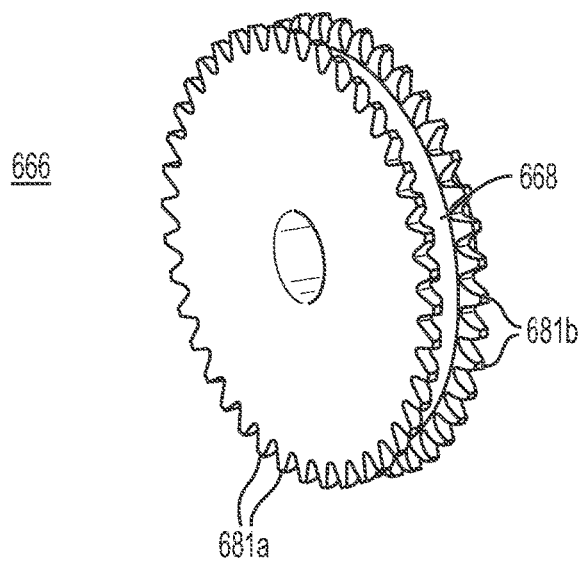
FIG. 14 illustrates an exemplary barrel having two sets of teeth.
Figure 15:
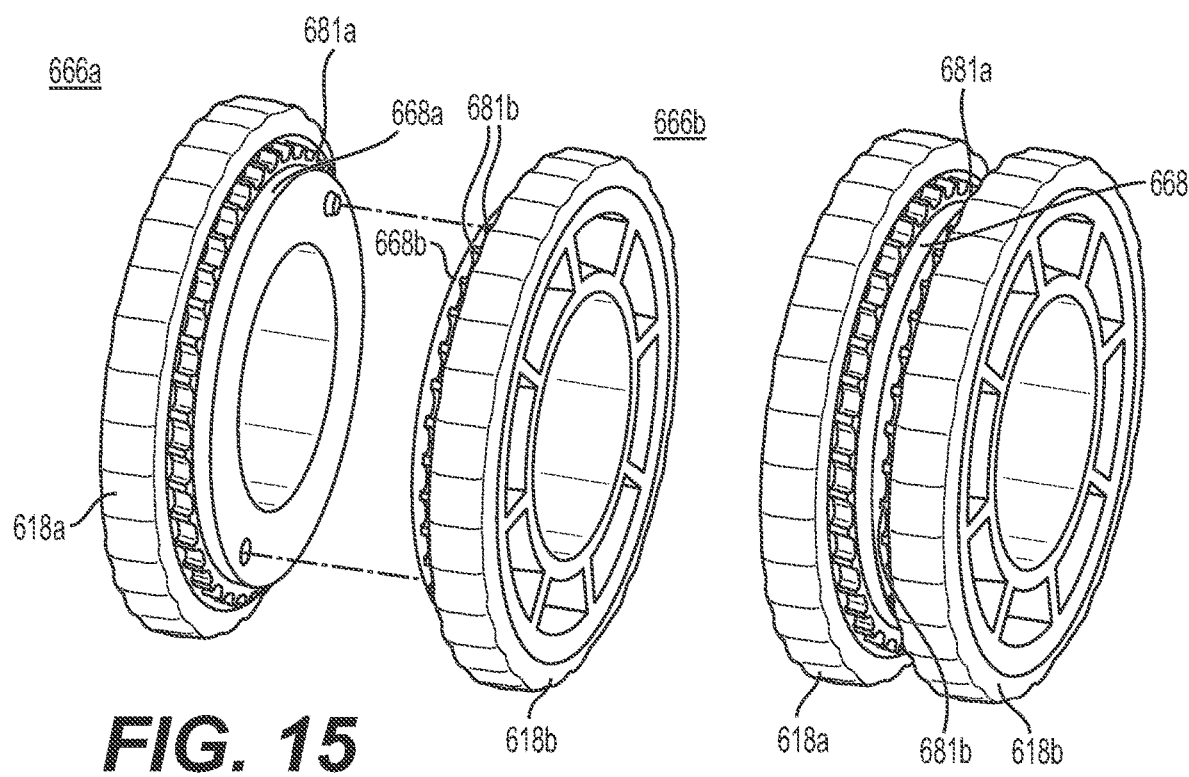
FIG. 15 illustrates a modular thumbwheel assembly according to principles described herein.

FIG. 14 illustrates an exemplary barrel 666 having two sets of teeth 681 with grooves therebetween. Between the two sets of teeth 681, which are arranged around the circumference of a circular cross section, is a surface 668 spacing the sets of teeth 681 apart from one another. As illustrated, the surface is smooth, but is not so limited. Moreover, although a surface is illustrated, the surface is not necessary. The teeth may be spaced apart merely be separating two disks with teeth and/or grooves on the periphery an appropriate distance apart, perhaps with both disks mounted on common axle (not shown). As discussed in detail, above, the barrel assembly 666 may be unitary, or may be unitary with the thumbwheels (not shown in FIG. 14). As illustrated in FIG. 15, the thumbwheel assembly with the barrel 666 may modular such that a first lateral portion of the barrel 666a and a first lateral portion of the thumbwheel 618a may be unitary and fit together with another unitary piece comprising as second lateral portion of the barrel 666b and a second lateral portion of the thumbwheel 618b. The lateral parts thumbwheel assembly may also include surfaces 668a and 668b that when fitted together form a surface to allow for spacing of the sets of teeth apart from one another.

Figure 16:
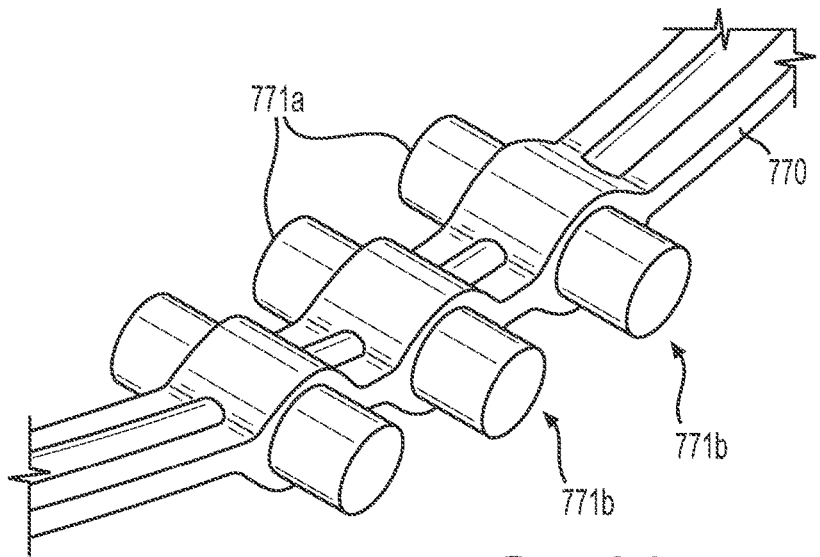
FIG. 16 illustrates an exemplary timing belt with timing belt teeth.

An exemplary timing belt with timing belt teeth are illustrated in FIG. 16. A timing belt for use with the barrel thus described has a plurality of protrusions on opposite sides of the belt, for example, extending perpendicular to a pitch axis of the belt. The belt shown in FIG. 16 is exemplary only, as it only shows three sets of teeth, but the belt is designed to have teeth along enough of the belt to sufficiently deploy the stent.

Figure 17:
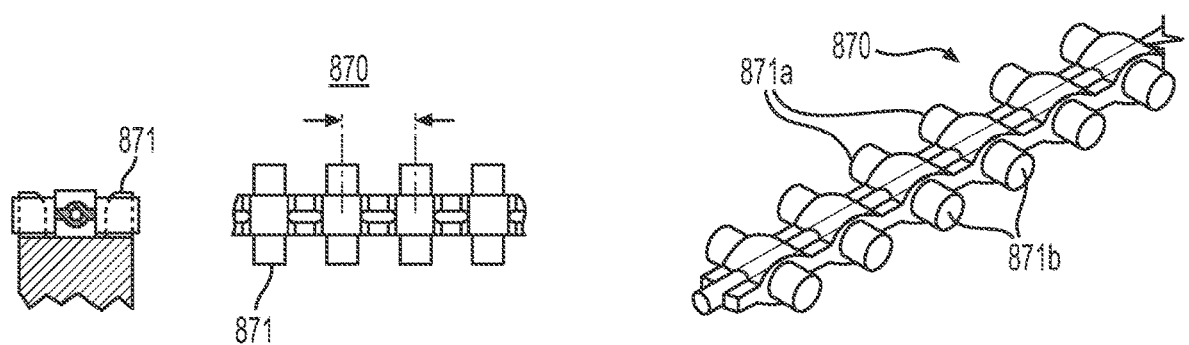
FIG. 17 illustrates an exemplary timing belt with timing belt teeth.

Exemplary belt teeth are shown in FIG. 17. As illustrated in FIG. 17, exemplary belt teeth may have a cylindrical shape with a flat top, e.g., trapezoidal cross-section, to allow for engagement with the barrel teeth. Although a trapezoidal cross section is shown, the teeth are not so limited and may be of any cross section that may engage with the barrel teeth sufficiently to allow belt movement to be actuated by barrel rotation. Other possible shapes, without limitation, include: without limitation, rounded, trapezoidal, cylindrical, diamond, square, triangular or any variation thereof.

FIG. 18(*a*) illustrates an idler 1182 that may be used with the posi-drive belt illustrated in FIG. 17. FIG. 18(*b*) illustrates a cross-section of the example idler pulley of FIG. 18(*a*) with the posi-drive belt.

Figure 19:
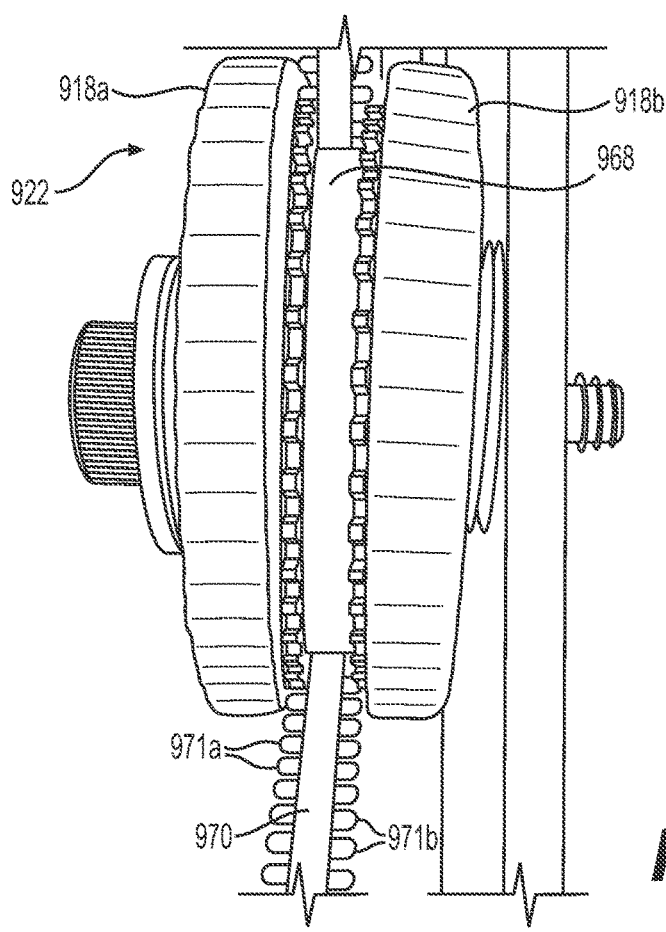
FIG. 19 shows a prototype thumbwheel/barrel assembly with a timing belt.

FIG. 19 shows a prototype thumbwheel/barrel assembly 922 having a cylindrical core 968 and thumbwheel portions 918 with a timing belt 970 having protrusions 971 on two edges of the timing belt 970, such as a single core posi-drive belt. A cylindrical core 968 can be seen between two sets of teeth/grooves 981.

FIGS. 20 and 21 illustrate an alternative type of posi-drive belt 1171 that could be used in the delivery assembly according to principles described herein. The illustrated posi-drive belt 1170 is "twin core" such that there is a recess or opening 1177 between each "crossbar" or tooth 1171 of the belt. The thumbwheel assembly and pulleys described herein may be adapted to engage the openings between the teeth of the belt to perform the movement described herein without impacting the overall function of the delivery device.

Figure 22:
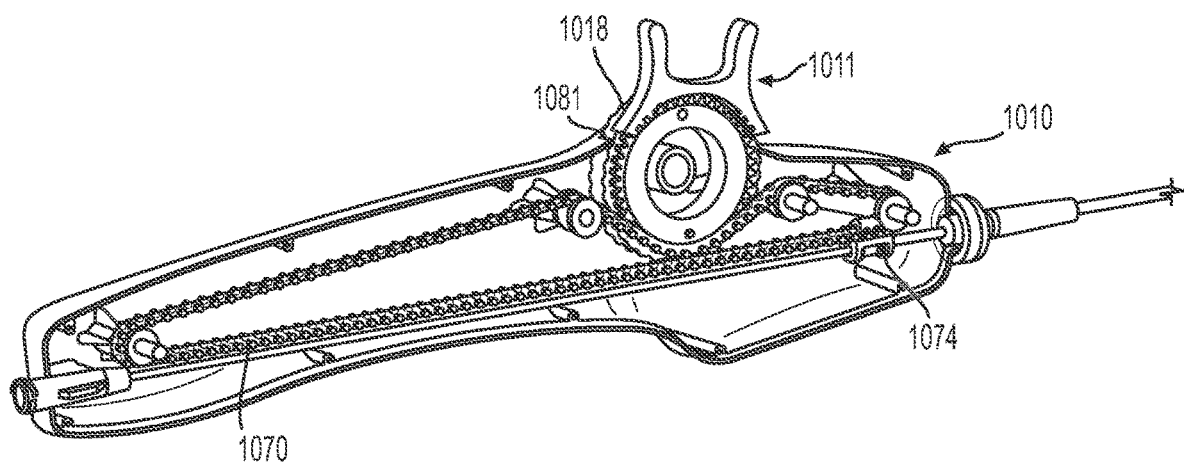
FIG. 22 illustrates a handle according to principles described herein.
Figure 23:
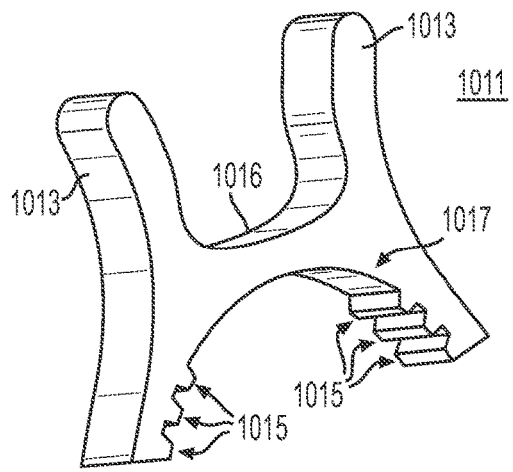
FIG. 23 shows an exemplary thumbwheel lock for use with the handle described herein.

FIG. 22 is a cross-sectional view of an exemplary handle 1010 according to principles described herein in combination with an exemplary thumbwheel lock 1011 and an exemplary timing belt link 1074. FIG. 23 shows an exemplary thumbwheel lock 1011 for use with the handle 1010 described herein. As shown, the exemplary thumbwheel lock 1011 is a levered lock that can be pinched to disengage a portion of the lock 1011 from the barrel teeth 1081. More particularly, the thumbwheel lock 1011 includes a plurality of teeth 1015 (which may be integral to or unitary with the thumbwheel lock or otherwise fixed to the thumbwheel lock 1011) that correspond to barrel teeth or to teeth on the surface of the thumbwheel (not shown). The exemplary thumbwheel lock 1011 includes two "lever" arms 1013 connected by a pivot bar 1016. The pivot bar 1016 provides pivot or fulcrum points for each of the lever arms 1013. One end of each lever arm 1013 includes teeth 1015 to engage a corresponding structure on the thumbwheel assembly 1018 of the handle 1010. The pivot/lever arms 1013 have sufficient spring force to clamp onto the thumbwheel assembly 1018 and be held in place by the engagement of the teeth 1015 of the thumbwheel lock 1011 and the thumbwheel assembly teeth 1081. The other ends of each of the lever arms 1013 has a sufficient length and width to allow them to be grasped and pinched together to cause the teeth 1015 of the thumbwheel lock 1013 to move away from the corresponding structure on the thumbwheel assembly 1018 (e.g., disengage from the thumbwheel assembly barrel teeth 1081) and thus be removed from the handle 1010 to allow the thumbwheel assembly 1018 to be actuated or rotated.

Figure 24:
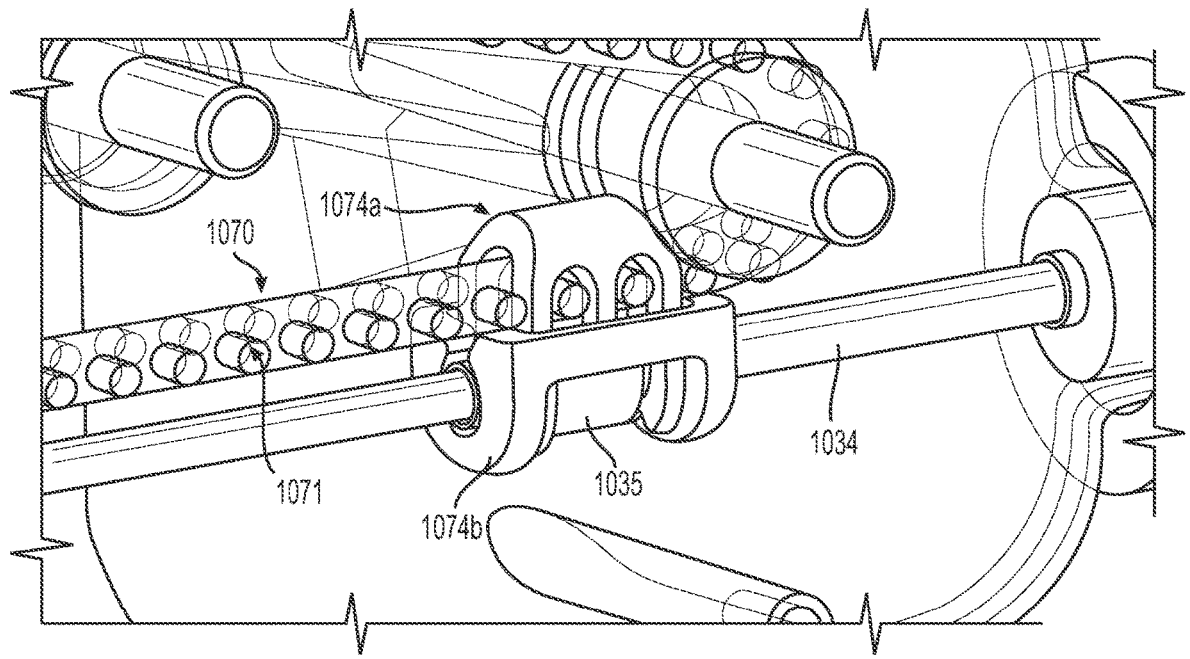
FIG. 24 illustrates an exemplary timing belt link for use with a posi-drive belt.

FIG. 24 illustrates an exemplary timing belt link 1074 for use with a posi-drive belt 1070. As illustrated, the exemplary timing belt link 1074 comprises two parts 1074a and 1074b that can be snapped together. Each part may be injection molded or formed by any appropriate process. The first part 1074a fits over the timing belt teeth 1071 of the timing belt 1070 and snaps around the outer-sheath 1034, trapping a cylindrical feature 1035 affixed to or integral to the outer-sheath 1034. The cylindrical feature 1035 may be integral to the outer sheath 1034 or otherwise affixed to the outer sheath 1034 such that the outer sheath 1034 may move with the movement of the cylindrical feature 1035. The second part 1074b snaps onto the outer sheath 1034 from below to create support system around the first part 1074a to provide rigidity. The second part 1074b provides the strength necessary to withstand deployment forces. The intent is of this design is to allow rotation of the outer sheath 1034 with respect to the belt 1070. According to an aspect of the present design, there is clearance between the timing belt link parts 1074a and 1074b and the outer sheath 1034 and the cylindrical feature 1035 to allow the outer sheath 1034 to spin freely without significant interference from the timing belt link 1074 yet allow linear movement of the timing belt link 1074 to cause movement of the outer sheath 1034 for deployment of the stent (not shown). Such movement is caused by the "entrapment" of the cylindrical feature 1035 by the timing belt link 1074. Thus, the system may remain functional when the distal end of the catheter is fixed and the proximal end (handle) is fully rotated 360° about the axis of the catheter (not shown).

Figure 25:
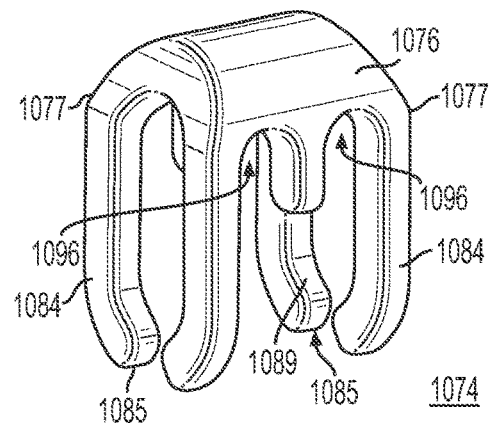
FIG. 25 illustrates an exemplary embodiment of the first part of the timing belt link of FIG. 24.

FIG. 25 illustrates an exemplary embodiment of the first part 1074a of the timing belt link 1074a of FIG. 24. The first part 1074a includes an upper body portion 1076; extension arms 1084 extending in a common direction from the upper body portion 1076 and engagement grooves 1096 complimentary to the teeth 1071 of the timing belt 1070. As illustrated, each extension arm 1084 extends from a corner 1077 of the upper body portion 1076, but this the design is not so limited. Distal ends 1085 of the extension arms 1084 may be curved so as to engage around the cylindrical outer sheath 1034, e.g. to provide a rough interference or snap fit. In the illustrated embodiment, there are four extension arms 1084, each extending from a corner 1077 of the upper body portion 1076. The upper body portion 1076 has a long dimension 1087 and a short dimension 1088, where the long dimension 1087 is parallel to the axial direction of the outer sheath 1034 when engaged with the outer sheath 1034 and the short dimension 1088 is roughly perpendicular to the axial direction of the outer sheath 1034 when engaged with the outer sheath 1034. In the exemplary embodiment shown, the engagement grooves 1096 are formed along the long dimension 1087 such that there are at least two grooves 1096 between to extension arms 1085 on one of the long dimensions 1087 of the upper body portion 1076. The grooves 1096 illustrated are U-shaped, such that when there are two such grooves 1096, there is a protrusion 1089 from the upper body 1076 at a location between corners 1077 of the upper body 1076 along the long dimension 1087 of the upper body 1076 forming two grooves 1096. While two grooves 1096 are illustrated, more grooves can be formed by more protrusions from the upper body such that more than two linearly adjacent belt teeth can be engaged. Also, there may be protrusions extending from both long edges/dimensions of the upper body such that grooves on both sides of a posi-drive belt can be engaged. In the presently illustrated embodiment, a longitudinal cross-section of the upper body 1076 may be U-shaped to fit over the outer sheath 1034.

Although not illustrated, the positioning of the extension arms is not limited to being at the corners of the upper body. In other words, as long as the extension arms are sufficient to fit around the outer sheath and grooves to engage the timing belt, the position from which they extend from the outer body can vary. For example, the extension arms may extend from a mid-point of the long dimension of the upper body, while the protrusions may extend from the corner 1077 or end regions of the upper body. Additional protrusions may extend from upper body to allow for additional timing belt teeth to be engaged by the upper body. The timing belt link 1074 may include only the first part but may further include a second part to provide additional strength to the assembly, e.g., to withstand deployment forces.

Figure 26:
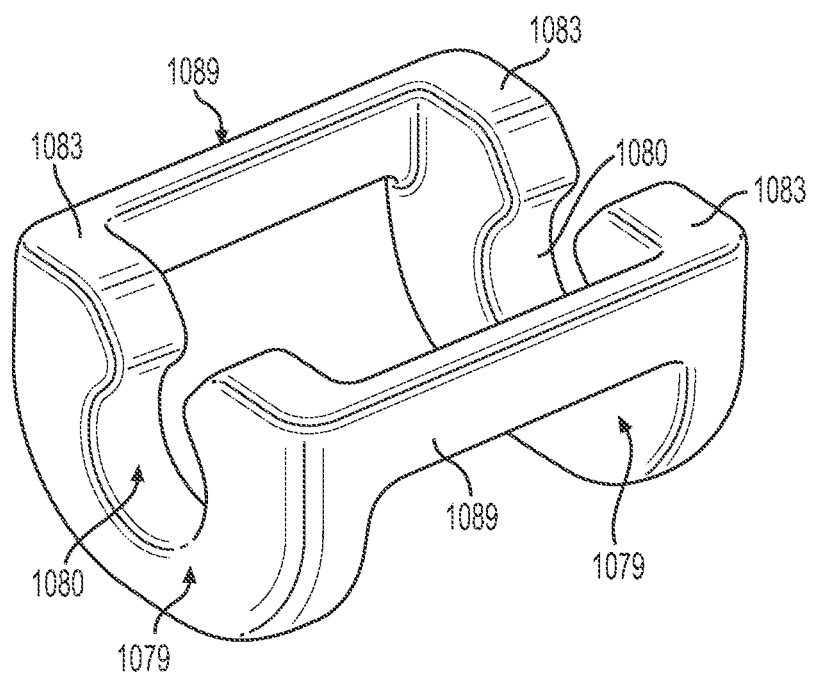
FIG. 26 illustrates an exemplary embodiment of the second part of the timing belt link of FIG. 24.

As shown in FIG. 26, an exemplary second part 1074b of may include a lower body portion 1075 having two U-shaped end pieces 1079 having a substantially circular center cut out 1080 sized to receive the circumference of the outer sheath 1034. The ends 1083 of each "U" are separated by a distance less than the outer diameter of the outer sheath 134 such that the outer sheath 134 can be pushed into the substantially circular center cut out 1080 of the "U" shaped end 1079. The U-shaped ends 1079 are connected by two upper side rails 1089 extending between upper parts of each of the "U"s 1079 to connect the two end pieces 1079.

The outer sheath 1034 can thus be coupled to the drive belt 1070 by the first part 1074a of the timing link 1074 extending over an upper portion of the outer sheath 1034 with the extension arm ends 1085 extending under a lower portion of the outer sheath 1034. The second part 1074b of the timing belt link 1074 is located over the extension arms 1084 of the first part and snap fit around the outer sheath 1034 by inserting the outer sheath 1034 into the substantially circular center cut outs 1080 of the U-shaped ends 1079 of the second part 1074b. The outer sheath 1034 may further include a cylindrical body 1035 sized to be between the extension arms 1085 of the upper body 1076 when the upper body 1076 is on the outer sheath 1034. For example, the cylindrical body 1035 may be permanently fixed to the outer sheath 1034 and thus be engaged by the timing belt link 1074 to hold the timing belt link 1074 in appropriate position with respect to the outer sheath 1034.

Figure 27:
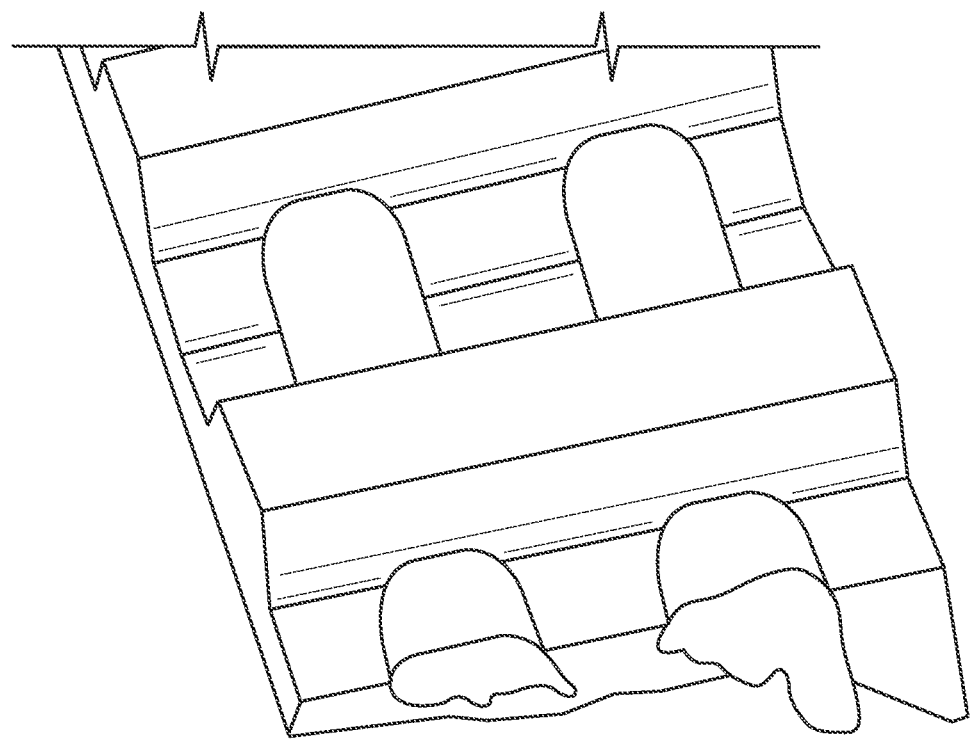
FIGS. 27, 28 and 29 are photographs showing the chord structure of an example posi-drive belt, which may be used in a delivery device according to principles described herein.
Figure 28:
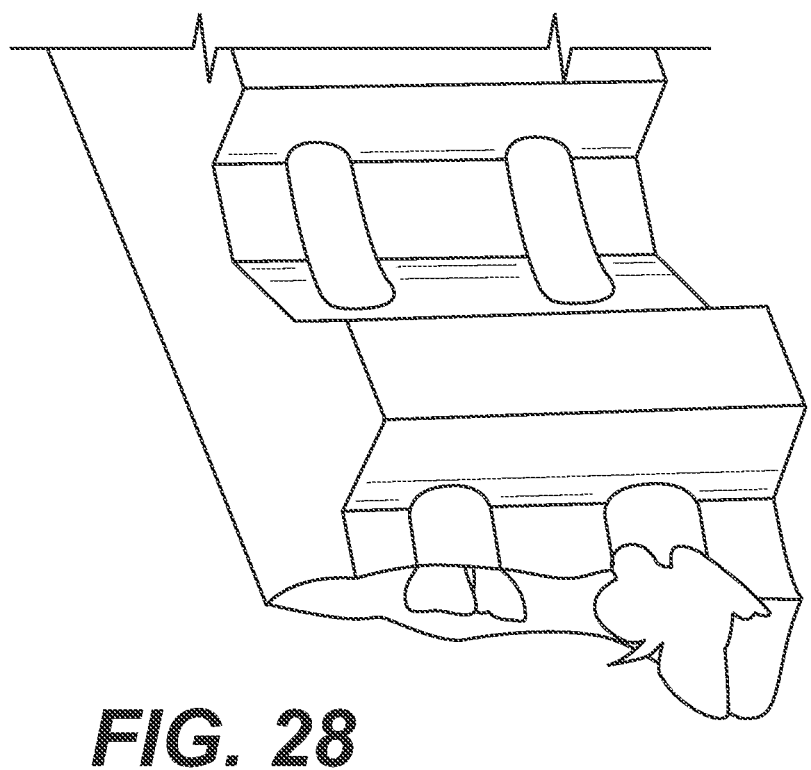
Figure 29:
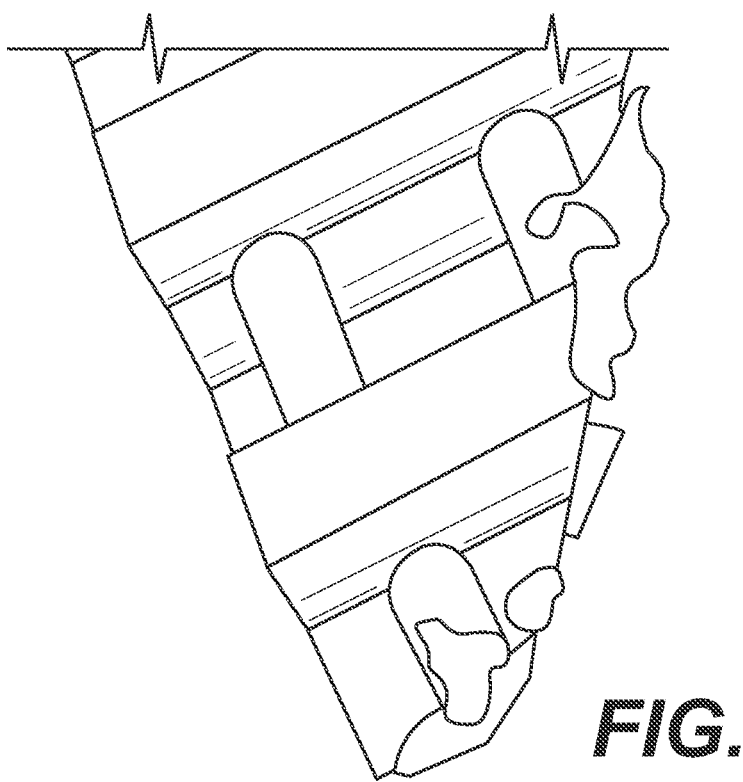

FIGS. 27, 28 and 29 are photographs showing the chord structure of an example posi-drive belt, which may be used in a delivery device according to principles described herein.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments but should be defined only in accordance with the following claims and their equivalents.

What is claimed is:

1. A method of delivering a medical device to a body using a delivery device comprising a catheter having three concentric shafts including an inner core, an outer sheath over the inner core and an outer support shaft; a timing belt having a first plurality of belt teeth and a second plurality of belt teeth; a timing belt link coupled to the outer sheath such that movement of the timing belt link causes movement of the outer sheath; a barrel having barrel teeth corresponding to at least one of the first plurality of belt teeth and the second plurality of belt teeth; a thumbwheel coupled to the barrel such that rotation of the thumbwheel causes movement of the barrel such that the barrel teeth engage at least one of the first plurality of belt teeth and the second plurality of belt teeth to cause movement of the timing belt causing movement of the outer sheath; and the medical device over an outer diameter of the inner core; the method comprising:

rotating the thumbwheel in a predetermined direction to cause the timing belt to move in direction associated with the predetermined direction of thumbwheel rotation to cause the timing belt link to move the outer sheath in a desired direction; and deploying the medical device from a distal end of the inner core to the body as the outer sheath moves in the desired direction.

2. The method of claim 1, wherein the three concentric shafts comprise:

the inner core sized to receive the medical device thereon;

the outer sheath sized to receive the medical device in an unexpanded state on the inner core therein and to hold the medical device, the outer sheath translatable coaxially over the inner core; and the outer support shaft at least partially extending over the inner core and the outer sheath.

3. The method of claim 1, wherein the thumbwheel is rotatable in a forward direction and a reverse direction such that the outer sheath translates in first direction when the thumbwheel is rotated in the forward direction and the outer sheath translates in a second direction when the thumbwheel is rotated in the reverse direction.

4. The method of claim 1, wherein the timing belt is a continuous loop.

5. The method of claim 1, wherein the first plurality of belt teeth protrudes in a first direction from the timing belt and the second plurality of belt teeth protrudes in a second direction from the timing belt.

6. The method of claim 1, wherein the first plurality of belt teeth protrudes in a first direction from the timing belt and the second plurality of belt teeth protrudes in a second direction from the timing belt.

7. The method of claim 6, wherein the first direction is different from the second direction.

8. The method of claim 6, wherein the first direction is opposite the second direction.

9. The method of claim 1, wherein the thumbwheel comprises a first wheel part having a first thumbwheel part and a first barrel part, the first barrel part having a first set of grooves at a periphery thereof; and a second wheel part having a second thumbwheel part and a second barrel part having a second set of grooves at a periphery thereof, the first wheel part and the second wheel part configured to be fitted together.

10. The method of claim 9, further comprising disengaging from the thumbwheel prior to rotating the thumbwheel, a thumbwheel lock comprising at least two pivot arms, at least one of the pivot arms including a plurality of engagement teeth corresponding to the at least one of the first set of grooves and the second set of grooves, the pivot arms having a spring force with respect to one another such that adjacent ends of the pivot arms are biased toward one another.

11. The method of claim 1, wherein the first plurality of belt teeth correspond to the first set of grooves and the second plurality of belt teeth correspond to the second set of grooves such that that rotation of the thumbwheel causes movement of the barrel such that at least one of the first set of grooves and the second set of grooves engage at least one of the first plurality of the belt teeth and the second plurality of belt teeth to cause movement of the timing belt causing movement of the outer sheath.

* * * * *